(12) United States Patent (10) Patent No.: US 8,728,477 B2
Kadouche et al. (45) Date of Patent: May 20, 2014

(54) NUCLEOTIDE AND PROTEIN SEQUENCES OF AN ANTIBODY DIRECTED AGAINST AN EPITOPE COMMON TO HUMAN ACIDIC AND BASIC FERRITINS, MONOCLONAL ANTIBODIES OR ANTIBODY-LIKE MOLECULES COMPRISING THESE SEQUENCES AND USES THEREOF

(75) Inventors: Jean Kadouche, Paris (FR); Emmanuelle Sabbah-Petrover, Paris (FR); Olivier Chose, Suresnes (FR)

(73) Assignee: Immune Pharmaceuticals Ltd., Herzlia (IL)

( * ) Notice: Subject to any disclaimer, the term of this patent is extended or adjusted under 35 U.S.C. 154(b) by 1030 days.

(21) Appl. No.: 11/902,194

(22) Filed: Sep. 19, 2007

(65) Prior Publication Data

US 2009/0074657 A1 Mar. 19, 2009

(51) Int. Cl.
*A61K 39/395* (2006.01)
*C07K 16/18* (2006.01)
*A61K 51/10* (2006.01)
*A61K 39/00* (2006.01)
*C07K 16/30* (2006.01)

(52) U.S. Cl.
CPC ........... *C07K 16/18* (2013.01); *C07K 2317/732* (2013.01); *A61K 51/1057* (2013.01); *A61K 2039/505* (2013.01); *C07K 16/303* (2013.01)
USPC ............... 424/155.1; 424/145.1; 424/1.49; 424/181.1

(58) Field of Classification Search
None
See application file for complete search history.

(56) References Cited

U.S. PATENT DOCUMENTS

| 5,585,089 | A | * | 12/1996 | Queen et al. | 424/133.1 |
| 5,859,205 | A | * | 1/1999 | Adair et al. | 530/387.3 |
| 6,015,555 | A | * | 1/2000 | Friden | 424/133.1 |
| 2002/0106324 | A1 | * | 8/2002 | Kadouche et al. | 424/1.49 |

FOREIGN PATENT DOCUMENTS

| EP | 1 563 851 A | 8/2005 |
| WO | WO 01/52889 A | 7/2001 |
| WO | WO 2007/034479 A | 3/2007 |

OTHER PUBLICATIONS

Chothia et al., J Mol Biol. Aug. 20, 1987;196(4):901-17.*
Portolano et al., J Immunol. Feb. 1, 1993;150(3):880-7.*
Eduardo Padlan, Mol Immunol. Feb. 1994;31(3):169-217.*
Vajdos et al., J Mol Biol. Jul. 5, 2002;320(2):415-28.*
International Search Report, dated Jul. 1, 2008, issued in connection with Counterpart International Application No. PCT/IB2007/003786.

Sabbah, et al., "In vitro and in vivo comparison of DTPA- and DOTA-conjugated antiferritin monoclonal antibody for imaging and therapy of pancreatic cancer," *Nuclear Medicine and Biology*, vol. 34, pp. 293-304, 2007.
Goldstein, et al., "The design and evaluation of a novel targeted drug delivery system using cationic emulsion-antibody conjugates," *Journal of Controlled Release*, vol. 108, pp. 418-432, 2005.
Vriesendorp, et al., "Recurrence of Hodgkin's Disease after Indium-111 and Yttrium-90 Labeled Antiferritin Administration," The American Cancer Society *Cancer Supplement*, vol. 80, No. 12, pp. 2721-2727, Dec. 15, 1997.
Cooper, Maggie S., et al., "Conjugation of chelating agents to proteins and radiolabeling with trivalent metallic isotopes", *Nature Protocols*, vol. 1, No. 1, pp. 314-317, 2006.
Drysdale, James W. et al., "Human Isoferritins in Normal and Disease States", *Semin Hematol.*, vol. 14, No. 1, pp. 71-88, 1977.
Eshhar, Zelig et al., "Ferritin, a Hodgkin's Disease Associated Antigen", *PNAS U.S.A.*, vol. 71, No. 10, pp. 3956-3960, 1974.
Guener, G. et al., "Cytosol and serum ferritin in breast carcinoma", *Cancer Letter*, vol. 67, No. 2-3, pp. 103-112, 1992.
Kadouche, De Jean et al., "IMMUNOLOGIE—Analyse de differentes isoferritines par des anticorps monoclonaux [Analysis of various isoferritins with monoclonal antibodies]", *C.R. Acad. Sc. Paris*, vol. 295, No. 6, pp. 443-448, 1982.
Marcus, Donald N. et al., "Isolation of Ferritin from Human Mammary and Pancreatic Carcinomas by Means of Antibody Immunoadsorbents", *Arch Biochem Biophys.*, vol. 162, No. 2, pp. 493-501, 1974.
Meares, Claude F. et al., "Conjugation of Antibodies with Bifunctional Chelating Agents: Isothiocyanate and Bromoacetamide Reagents, Methods of Analysis, and Subsequent Addition of Metal Ions", *Analytcal Biochemistry*, vol. 142, No. 1, pp. 68-78, 1984.
Weinstein, Robert E. et al., "Tissue ferritin concentration and prognosis in carcinoma of the breast", *Breast Cancer Res. Treat.*, vol. 14, No. 3, pp. 349-353, 1989.
Kettleborough et al. "Humanization of a mouse monoclonal antibody by CDR-Grafting: The importance of framework residues on loop conformation" Protein Eng. Oct. 1991;4(7):773-83.
Leveque et al. "Pharmacokinetics of therapeutic monoclonal antibodies used in oncology" Anticancer Res. May-Jun. 2005;25(3c):2327-43.
Ono et al. "Common epitopes in human isoferritins characterized by murine monoclonal antibodies" J Biochem. Jan. 1986;99(1):269-79.
Tabrizi et al. "Biodistribution mechanisms of therapeutic monoclonal antibodies in health and disease" AAPS J. Mar. 2010;12(1):33-43.

* cited by examiner

*Primary Examiner* — Zachary Skelding
(74) *Attorney, Agent, or Firm* — Mark S. Cohen; Pearl Cohen; Zedek Latzer Baratz LLP

(57) ABSTRACT

The present invention is directed to monoclonal, chimeric or humanized, antibodies or antibody-like molecules that recognize an epitope common to human acidic and basic isoferritins. The anti-ferritin antibodies or antibody-like molecules can be used in pharmaceutical compositions for immunotherapy or radioimmunotherapy to target various cancer cells in a mammal. A method for delivering anti-ferritin antibodies or antibody-like molecules to cancerous lymph cells, pancreatic cells, lymphatic endothelium cells, and liver cells is also disclosed, as well as methods for treating pancreatic cancer, hepatocellular carcinomas, Kaposi's sarcoma and Hodgkin's lymphoma.

51 Claims, 13 Drawing Sheets

```
CAA ATT GTT CTC ACC CAG TCT CCA GCA ATC CTG TCT GCA TCT CTA GGG     48
 Q   I   V   L   T   Q   S   P   A   I   L   S   A   S   L   G     16
                            FR1

GAG GAG ATC ACC CTA ACC TGC AGT GCC AGC TCG AGT GTA ACT TTC ATG     96
 E   E   I   T   L   T   C   S   A   S   S   S   V   T   F   M     32
            FR1                              CDR1

CAC TGG TAC CAG CAG AAG TCA GGC ACT TCT CCC AAA CTC TTG ATT TAT    144
 H   W   Y   Q   Q   K   S   G   T   S   P   K   L   L   I   Y     48
                            FR2

ACC ACA TCC AAC CTG GCT TCT GGA GTC CCT TCT CGC TTC AGT GGC AGT    192
 T   T   S   N   L   A   S   G   V   P   S   R   F   S   G   S     64
      CDR2                    FR3

GGG TCT GGG ACC TTT TAT TCT CTC ACA ATC AGC AGT GTG GAG GCT GAA    240
 G   S   G   T   F   Y   S   L   T   I   S   S   V   E   A   E     80
                            FR3

GAT GCT GCC GAT TAT TAC TGC CAT CAG TGG AGT AGT TAT CCC ACG TTC    288
 D   A   A   D   Y   Y   C   H   Q   W   S   S   Y   P   T   F     96
          FR3                         CDR3

GGC TCG GGG ACA AAG TTG GAA ATA AAA CGG                            318
 G   S   G   T   K   L   E   I   K   R                             106
            FR4
```

Fig. 1

```
   Q   V   Q   L   K   E   S   G   P   G   L   V   A   P   S   Q   S   L       18
  CAG GTG CAG CTG AAG GAG TCA GGA CCT GGC CTG GTG GCA CCC TCA CAG AGC CTG      54
                                       FR1

S   I   T   C   T   V   S   G   F   S   L   S   R   Y   S   V   H   W       36
  TCC ATC ACA TGC ACT GTC TCT GGG TTC TCA TTA TCC AGA TAT AGT GTA CAC TGG     108
              FR1                     CDR1                        FR2

V   R   Q   P   P   G   K   G   L   E   W   L   G   T   I   W   G   G       54
  GTT CGC CAG CCT CCA GGA AAG GGT CTG GAG TGG CTG GGA ACG ATA TGG GGT GGT     162
                       FR2                                    CDR2

G   S   T   D   Y   N   S   V   L   K   S   R   L   S   I   S   K   D       72
  GGA AGC ACA GAC TAT AAC TCA GTT CTC AAA TCC AGA CTG AGC ATC AGC AAG GAC     216
         CDR2                                 FR3

N   S   K   S   Q   V   L   L   K   V   N   S   L   Q   T   D   D   T       90
  AAC TCC AAG AGC CAA GTT TTG TTA AAA GTG AAC AGT CTA CAA ACT GAT GAC ACA     270
                                       FR3

A   I   Y   Y   C   A   S   G   P   Y   Y   Y   T   M   D   Y   W   G      108
  GCC ATA TAT TAC TGT GCC AGT GGT CCT TAT TAC TAT ACT ATG GAC TAC TGG GGT     324
              FR3                       CDR3

Q   G   T   S   V   T   V   S   S                                          117
  CAA GGA ACC TCA GTC ACC GTC TCC TCA                                         351
              FR4
```

Fig. 2

| | | | | | | | | | | | | | | | | |
|---|---|---|---|---|---|---|---|---|---|---|---|---|---|---|---|---|
| GCT | AGC | ACC | AAG | GGC | CCA | TCG | GTC | TTC | CCC | CTG | GCA | CCC | TCC | TCC | AAG | 48 |
| A | S | T | K | G | P | S | V | F | P | L | A | P | S | S | K | 16 |
| AGC | ACC | TCT | GGG | GGC | ACA | GCG | GCC | CTG | GGC | TGC | CTG | GTC | AAG | GAC | TAC | 96 |
| S | T | S | G | G | T | A | A | L | G | C | L | V | K | D | Y | 32 |
| TTC | CCC | GAA | CCG | GTG | ACG | GTG | TCG | TGG | AAC | TCA | GGC | GCC | CTG | ACC | AGC | 144 |
| F | P | E | P | V | T | V | S | W | N | S | G | A | L | T | S | 48 |
| GGC | GTG | CAC | ACC | TTC | CCG | GCT | GTC | CTA | CAG | TCC | TCA | GGA | CTC | TAC | TCC | 192 |
| G | V | H | T | F | P | A | V | L | Q | S | S | G | L | Y | S | 64 |
| CTC | AGC | AGC | GTG | GTG | ACC | GTG | CCC | TCC | AGC | AGC | TTG | GGC | ACC | CAG | ACC | 240 |
| L | S | S | V | V | T | V | P | S | S | S | L | G | T | Q | T | 80 |
| TAC | ATC | TGC | AAC | GTG | AAT | CAC | AAG | CCC | AGC | AAC | ACC | AAG | GTG | GAC | AAG | 288 |
| Y | I | C | N | V | N | H | K | P | S | N | T | K | V | D | K | 96 |
| AAA | GTT | GAG | CCC | AAA | TCT | TGT | GAC | AAA | ACT | CAC | ACA | TGC | CCA | CCG | TGC | 336 |
| K | V | E | P | K | S | C | D | K | T | H | T | C | P | P | C | 112 |
| CCA | TGC | TAA | | | | | | | | | | | | | | 345 |
| P | C | * | | | | | | | | | | | | | | 115 |

Fig. 3

```
GCT AGC ACC AAG GGC CCA TCG GTC TTC CCC CTG GCA CCC TCC TCC AAG    48
 A   S   T   K   G   P   S   V   F   P   L   A   P   S   S   K    16

AGC ACC TCT GGG GGC ACA GCG GCC CTG GGC TGC CTG GTC AAG GAC TAC    96
 S   T   S   G   G   T   A   A   L   G   C   L   V   K   D   Y    32

TTC CCC GAA CCG GTG ACG GTG TCG TGG AAC TCA GGC GCC CTG ACC AGC   144
 F   P   E   P   V   T   V   S   W   N   S   G   A   L   T   S    48

GGC GTG CAC ACC TTC CCG GCT GTC CTA CAG TCC TCA GGA CTC TAC TCC   192
 G   V   H   T   F   P   A   V   L   Q   S   S   G   L   Y   S    64

CTC AGC AGC GTG GTG ACC GTG CCC TCC AGC AGC TTG GGC ACC CAG ACC   240
 L   S   S   V   V   T   V   P   S   S   S   L   G   T   Q   T    80

TAC ATC TGC AAC GTG AAT CAC AAG CCC AGC AAC ACC AAG GTG GAC AAG   288
 Y   I   C   N   V   N   H   K   P   S   N   T   K   V   D   K    96

AAA GTT GAG CCC AAA TCT TGT GAC AAA ACT CAC ACA TGC CCA CCG TGC   336
 K   V   E   P   K   S   C   D   K   T   H   T   C   P   P   C   112

CCA GCA CCT GAA CTC CTG GGG GGA CCG TCA GTC TTC CTC TTC CCC CCA   384
 P   A   P   E   L   L   G   G   P   S   V   F   L   F   P   P   128

AAA CCC AAG GAC ACC CTC ATG ATC TCC CGG ACC CCT GAG GTC ACA TGC   432
 K   P   K   D   T   L   M   I   S   R   T   P   E   V   T   C   144

GTG GTG GTG GAC GTG AGC CAC GAA GAC CCT GAG GTC AAG TTC AAC TGG   480
 V   V   V   D   V   S   H   E   D   P   E   V   K   F   N   W   160

TAC GTG GAC GGC GTG GAG GTG CAT AAT GCC AAG ACA AAG CCG CGG GAG   528
 Y   V   D   G   V   E   V   H   N   A   K   T   K   P   R   E   176

GAG CAG TAC AAC AGC ACG TAC CGT GTG GTC AGC GTC CTC ACC GTC CTG   576
 E   Q   Y   N   S   T   Y   R   V   V   S   V   L   T   V   L   192

CAC CAG GAC TGG CTG AAT GGC AAG GAG TAC AAG TGC AAG GTC TCC AAC   624
 H   Q   D   W   L   N   G   K   E   Y   K   C   K   V   S   N   208

AAA GCC CTC CCA GCC CCC ATC GAG AAA ACC ATC TCC AAA GCC AAA GGG   672
 K   A   L   P   A   P   I   E   K   T   I   S   K   A   K   G   224

CAG CCC CGA GAA CCA CAG GTG TAC ACC CTG CCC CCA TCC CGG GAT GAG   720
 Q   P   R   E   P   Q   V   Y   T   L   P   P   S   R   D   E   240

CTG ACC AAG AAC CAG GTC AGC CTG ACC TGC CTG GTC AAA GGC TTC TAT   768
 L   T   K   N   Q   V   S   L   T   C   L   V   K   G   F   Y   256

CCC AGC GAC ATC GCC GTG GAG TGG GAG AGC AAT GGG CAG CCG GAG AAC   816
 P   S   D   I   A   V   E   W   E   S   N   G   Q   P   E   N   272

AAC TAC AAG ACC ACG CCT CCC GTG CTG GAC TCC GAC GGC TCC TTC TTC   864
 N   Y   K   T   T   P   P   V   L   D   S   D   G   S   F   F   288

CTC TAC AGC AAG CTC ACC GTG GAC AAG AGC AGG TGG CAG CAG GGG AAC   912
 L   Y   S   K   L   T   V   D   K   S   R   W   Q   Q   G   N   304

GTC TTC TCA TGC TCC GTG ATG CAT GAG GCT CTG CAC AAC CAC TAC ACG   960
 V   F   S   C   S   V   M   H   E   A   L   H   N   H   Y   T   320

CAG AAG AGC CTC TCC CTG TCT CCG GGT AAA TAA                        990
 Q   K   S   L   S   L   S   P   G   K   *                         330
```

Fig. 4

```
GCT AGC ACC AAG GGC CCA TCC GTC TTC CCC CTG GCG CCC TGC TCC AGG    48
 A   S   T   K   G   P   S   V   F   P   L   A   P   C   S   R    16

AGC ACC TCC GAG AGC ACA GCC GCC CTG GGC TGC CTG GTC AAG GAC TAC    96
 S   T   S   E   S   T   A   A   L   G   C   L   V   K   D   Y    32

TTC CCC GAA CCG GTG ACG GTG TCG TGG AAC TCA GGC GCC CTG ACC AGC   144
 F   P   E   P   V   T   V   S   W   N   S   G   A   L   T   S    48

GGC GTG CAC ACC TTC CCG GCT GTC CTA CAG TCC TCA GGA CTC TAC TCC   192
 G   V   H   T   F   P   A   V   L   Q   S   S   G   L   Y   S    64

CTC AGC AGC GTG GTG ACC GTG CCC TCC AGC AGC TTG GGC ACG AAG ACC   240
 L   S   S   V   V   T   V   P   S   S   S   L   G   T   K   T    80

TAC ACC TGC AAC GTA GAT CAC AAG CCC AGC AAC ACC AAG GTG GAC AAG   288
 Y   T   C   N   V   D   H   K   P   S   N   T   K   V   D   K    96

AGA GTT GAG TCC AAA TAT GGT CCC CCA TGC CCA TCA TGC CCA GCA CCT   336
 R   V   E   S   K   Y   G   P   P   C   P   S   C   P   A   P   112

GAG TTC CTG GGG GGA CCA TCA GTC TTC CTG TTC CCC CCA AAA CCC AAG   384
 E   F   L   G   G   P   S   V   F   L   F   P   P   K   P   K   128

GAC ACT CTC ATG ATC TCC CGG ACC CCT GAG GTC ACG TGC GTG GTG GTG   432
 D   T   L   M   I   S   R   T   P   E   V   T   C   V   V   V   144

GAC GTG AGC CAG GAA GAC CCC GAG GTC CAG TTC AAC TGG TAC GTG GAT   480
 D   V   S   Q   E   D   P   E   V   Q   F   N   W   Y   V   D   160

GGC GTG GAG GTG CAT AAT GCC AAG ACA AAG CCG CGG GAG GAG CAG TTC   528
 G   V   E   V   H   N   A   K   T   K   P   R   E   E   Q   F   176

AAC AGC ACG TAC CGT GTG GTC AGC GTC CTC ACC GTC CTG CAC CAG GAC   576
 N   S   T   Y   R   V   V   S   V   L   T   V   L   H   Q   D   192

TGG CTG AAC GGC AAG GAG TAC AAG TGC AAG GTC TCC AAC AAA GGC CTC   624
 W   L   N   G   K   E   Y   K   C   K   V   S   N   K   G   L   208

CCG TCC TCC ATC GAG AAA ACC ATC TCC AAA GCC AAA GGG CAG CCC CGA   672
 P   S   S   I   E   K   T   I   S   K   A   K   G   Q   P   R   224

GAG CCA CAG GTG TAC ACC CTG CCC CCA TCC CAG GAG GAG ATG ACC AAG   720
 E   P   Q   V   Y   T   L   P   P   S   Q   E   E   M   T   K   240

AAC CAG GTC AGC CTG ACC TGC CTG GTC AAA GGC TTC TAC CCC AGC GAC   768
 N   Q   V   S   L   T   C   L   V   K   G   F   Y   P   S   D   256

ATC GCC GTG GAG TGG GAG AGC AAT GGG CAG CCG GAG AAC AAC TAC AAG   816
 I   A   V   E   W   E   S   N   G   Q   P   E   N   N   Y   K   272

ACC ACG CCT CCC GTG CTG GAC TCC GAC GGC TCC TTC TTC CTC TAC AGC   864
 T   T   P   P   V   L   D   S   D   G   S   F   F   L   Y   S   288

AGG CTA ACC GTG GAC AAG AGC AGG TGG CAG GAG GGG AAT GTC TTC TCA   912
 R   L   T   V   D   K   S   R   W   Q   E   G   N   V   F   S   304

TGC TCC GTG ATG CAT GAG GCT CTG CAC AAC CAC TAC ACA CAG AAG AGC   960
 C   S   V   M   H   E   A   L   H   N   H   Y   T   Q   K   S   320

CTC TCC CTG TCT CTG GGT AAA TAA                                   981
 L   S   L   S   L   G   K   *                                    327
```

Fig. 5

```
ACG GTG GCT GCA CCA TCT GTC TTC ATC TTC CCG CCA TCT GAT GAG CAG    48
 T   V   A   A   P   S   V   F   I   F   P   P   S   D   E   Q    16

TTG AAA TCT GGA ACT GCC TCT GTT GTG TGC CTG CTG AAT AAC TTC TAT    96
 L   K   S   G   T   A   S   V   V   C   L   L   N   N   F   Y    32

CCC AGA GAG GCC AAA GTA CAG TGG AAG GTG GAT AAC GCC CTC CAA TCG   144
 P   R   E   A   K   V   Q   W   K   V   D   N   A   L   Q   S    48

GGT AAC TCC CAG GAG AGT GTC ACA GAG CAG GAC AGC AAG GAC AGC ACC   192
 G   N   S   Q   E   S   V   T   E   Q   D   S   K   D   S   T    64

TAC AGC CTC AGC AGC ACC CTG ACG CTG AGC AAA GCA GAC TAC GAG AAA   240
 Y   S   L   S   S   T   L   T   L   S   K   A   D   Y   E   K    80

CAC AAA GTC TAC GCC TGC GAA GTC ACC CAT CAG GGC CTG AGT TCG CCC   288
 H   K   V   Y   A   C   E   V   T   H   Q   G   L   S   S   P    96

GTC ACA AAG AGC TTC AAC AGG GGA GAG TGT TAA                       321
 V   T   K   S   F   N   R   G   E   C   *                        107
```

Fig. 6

```
ATG GAC ATG CGT GTG CCC GCT CAA CTC CTG GGC CTG CTG CTG CTC TGG    48
 M   D   M   R   V   P   A   Q   L   L   G   L   L   L   L   W    16

CTC CCA GGT GCG CGC TGT                                            66
 L   P   G   A   R   C                                             22
```

Fig. 7

```
ATG GAG TTC GGC CTG AGC TGG CTG TTC CTG GTG GCT ATT CTT AAG GGT    48
 M   E   F   G   L   S   W   L   F   L   V   A   I   L   K   G    16

GTC CAG TGT                                                        57
 V   Q   C                                                         19
```

Fig. 8

```
GCCAAAACAACAGCCCCATCGGTCTATCCACTGGCCCCTGTGTGTGGAGATACAACTGGCTCCTCGGTGA
CTCTAGGATGCCTGGTCAAGGGTTATTTCCCTGAGCCAGTGACCTTGACCTGGAACTCTGGATCCCTGTC
CAGTGGTGTGCACACCTTCCCAGCTGTCCTGCAGTCTGACCTCTACACCCTCAGCAGCTCAGTGACTGTA
ACCTCGAGCACCTGGCCCAGCCAGTCCATCACCTGCAATGTGGCCCACCCGGCAAGCAGCACCAAGGTGG
ACAAGAAAATTGAGCCCAGAGGGCCCACAATCAAGCCCTGTCCTCCATGCAAATGCCCAGCACCTAACCT
CTTGGGTGGACCATCCGTCTTCATCTTCCCTCCAAAGATCAAGGATGTACTCATGATCTCCCTGAGCCCC
ATAGTCACATGTGTGGTGGTGGATGTGAGCGAGGATGACCCAGATGTCCAGATCAGCTGGTTTGTGAACA
ACGTGGAAGTACACACAGCTCAGACACAAACCCATAGAGAGGATTACAACAGTACTCTCCGGGTGGTCAG
TGCCCTCCCCATCCAGCACCAGGACTGGATGAGTGGCAAGGAGTTCAAATGCAAGGTCAACAACAAAGAC
CTCCCAGCGCCCATCGAGAGAACCATCTCAAAACCCAAAGGGTCAGTAAGAGCTCCACAGGTATATGTCT
TGCCTCCACCAGAAGAAGAGATGACTAAGAAACAGGTCACTCTGACCTGCATGGTCACAGACTTCATGCC
TGAAGACATTTACGTGGAGTGGACCAACAACGGGAAAACAGAGCTAAACTACAAGAACACTGAACCAGTC
CTGGACTCTGATGGTTCTTACTTCATGTACAGCAAGCTGAGAGTGGAAAAGAAGAACTGGGTGGAAAGAA
ATAGCTACTCCTGTTCAGTGGTCCACGAGGGTCTGCACAATCACCACACGACTAAGAGCTTCTCCCGGAC
TCCGGGTAAATGAGCTCAGCACCCACAAAACTCTCAGGTCCAAAGAGACACCCACACTCATCTCCATGCT
TCCCTTGTATAAATAAAGCACCCAGCAATGCCTGGGACCATGTAA
```

Fig. 9A

```
AKTTAPSVYPLAPVCGDTTGSSVTLGCLVKGYFPEPVTLTWNSGSLSSGVHTFPAVLQSD
LYTLSSSVTVTSSTWPSQSITCNVAHPASSTKVDKKIEPRGPTIKPCPPCKCPAPNLLGG
PSVFIFPPKIKDVLMISLSPIVTCVVVDVSEDDPDVQISWFVNNVEVHTAQTQTHREDYN
STLRVVSALPIQHQDWMSGKEFKCKVNNKDLPAPIERTISKPKGSVRAPQVYVLPPPEEE
MTKKQVTLTCMVTDFMPEDIYVEWTNNGKTELNYKNTEPVLDSDGSYFMYSKLRVEKKNW
VERNSYSCSVVHEGLHNHHTTKSFSRTPGK
```

Fig. 9B

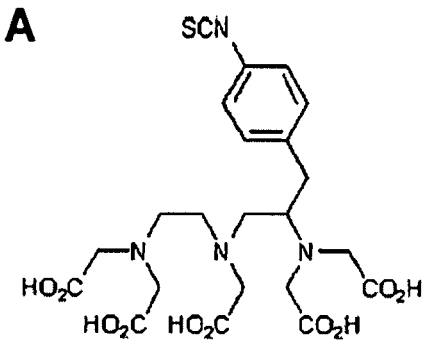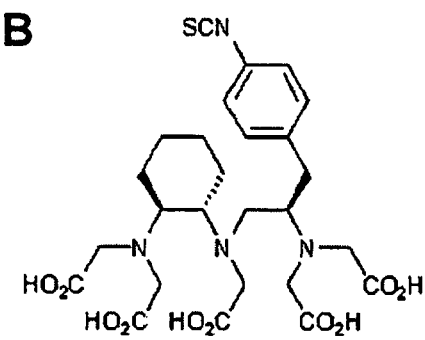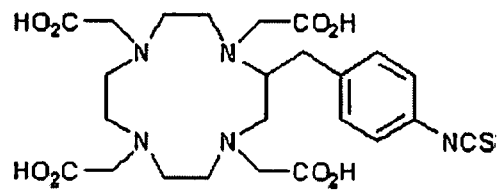
Fig. 10

SEQUENCE LISTING

```
<160> NUMBER OF SEQ ID NOS: 48

<210> SEQ ID NO 1
<211> LENGTH: 318
<212> TYPE: DNA
<213> ORGANISM: Mus musculus
<220> FEATURE:
```

```
<221> NAME/KEY: CDS
<222> LOCATION: (1)..(318)

<400> SEQUENCE: 1 caa att gtt ctc acc cag tct cca gca atc ctg tct gca tct cta ggg     48
Gln Ile Val Leu Thr Gln Ser Pro Ala Ile Leu Ser Ala Ser Leu Gly
  1               5                  10                  15 gag gag atc acc cta acc tgc agt gcc agc tcg agt gta act ttc atg     96
Glu Glu Ile Thr Leu Thr Cys Ser Ala Ser Ser Ser Val Thr Phe Met
             20                  25                  30 cac tgg tac cag cag aag tca ggc act tct ccc aaa ctc ttg att tat    144
His Trp Tyr Gln Gln Lys Ser Gly Thr Ser Pro Lys Leu Leu Ile Tyr
         35                  40                  45 acc aca tcc aac ctg gct tct gga gtc cct tct cgc ttc agt ggc agt    192
Thr Thr Ser Asn Leu Ala Ser Gly Val Pro Ser Arg Phe Ser Gly Ser
     50                  55                  60 ggg tct ggg acc ttt tat tct ctc aca atc agc agt gtg gag gct gaa    240
Gly Ser Gly Thr Phe Tyr Ser Leu Thr Ile Ser Ser Val Glu Ala Glu
 65                  70                  75                  80 gat gct gcc gat tat tac tgc cat cag tgg agt agt tat ccc acg ttc    288
Asp Ala Ala Asp Tyr Tyr Cys His Gln Trp Ser Ser Tyr Pro Thr Phe
                 85                  90                  95 ggc tcg ggg aca aag ttg gaa ata aaa cgg                            318
Gly Ser Gly Thr Lys Leu Glu Ile Lys Arg
            100                 105

<210> SEQ ID NO 2
<211> LENGTH: 106
<212> TYPE: PRT
<213> ORGANISM: Mus musculus

<400> SEQUENCE: 2

Gln Ile Val Leu Thr Gln Ser Pro Ala Ile Leu Ser Ala Ser Leu Gly
  1               5                  10                  15

Glu Glu Ile Thr Leu Thr Cys Ser Ala Ser Ser Ser Val Thr Phe Met
             20                  25                  30

His Trp Tyr Gln Gln Lys Ser Gly Thr Ser Pro Lys Leu Leu Ile Tyr
         35                  40                  45

Thr Thr Ser Asn Leu Ala Ser Gly Val Pro Ser Arg Phe Ser Gly Ser
     50                  55                  60

Gly Ser Gly Thr Phe Tyr Ser Leu Thr Ile Ser Ser Val Glu Ala Glu
 65                  70                  75                  80

Asp Ala Ala Asp Tyr Tyr Cys His Gln Trp Ser Ser Tyr Pro Thr Phe
                 85                  90                  95

Gly Ser Gly Thr Lys Leu Glu Ile Lys Arg
            100                 105

<210> SEQ ID NO 3
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 3 cag gtg cag ctg aag gag tca gga cct ggc ctg gtg gca ccc tca cag     48
Gln Val Gln Leu Lys Glu Ser Gly Pro Gly Leu Val Ala Pro Ser Gln
  1               5                  10                  15 agc ctg tcc atc aca tgc act gtc tct ggg ttc tca tta tcc aga tat     96
Ser Leu Ser Ile Thr Cys Thr Val Ser Gly Phe Ser Leu Ser Arg Tyr
             20                  25                  30
```

| | | | | | | | | | | | | |
|---|---|---|---|---|---|---|---|---|---|---|---|---|
| agt | gta | cac | tgg | gtt | cgc | cag | cct | cca | gga | aag | ggt | ctg | gag | tgg | ctg | 144 |
| Ser | Val | His | Trp | Val | Arg | Gln | Pro | Pro | Gly | Lys | Gly | Leu | Glu | Trp | Leu | |
| | | 35 | | | | 40 | | | | | 45 | | | | | |

```
agt gta cac tgg gtt cgc cag cct cca gga aag ggt ctg gag tgg ctg        144
Ser Val His Trp Val Arg Gln Pro Pro Gly Lys Gly Leu Glu Trp Leu
        35                  40                  45 gga acg ata tgg ggt ggt gga agc aca gac tat aac tca gtt ctc aaa        192
Gly Thr Ile Trp Gly Gly Gly Ser Thr Asp Tyr Asn Ser Val Leu Lys
 50                  55                  60 tcc aga ctg agc atc agc aag gac aac tcc aag agc caa gtt ttg tta        240
Ser Arg Leu Ser Ile Ser Lys Asp Asn Ser Lys Ser Gln Val Leu Leu
 65                  70                  75                  80 aaa gtg aac agt cta caa act gat gac aca gcc ata tat tac tgt gcc        288
Lys Val Asn Ser Leu Gln Thr Asp Asp Thr Ala Ile Tyr Tyr Cys Ala
                 85                  90                  95 agt ggt cct tat tac tat act atg gac tac tgg ggt caa gga acc tca        336
Ser Gly Pro Tyr Tyr Tyr Thr Met Asp Tyr Trp Gly Gln Gly Thr Ser
            100                 105                 110 gtc acc gtc tcc tca                                                    351
Val Thr Val Ser Ser
        115

<210> SEQ ID NO 4
<211> LENGTH: 117
<212> TYPE: PRT
<213> ORGANISM: Mus musculus

<400> SEQUENCE: 4

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ser Arg Tyr
                 20                  25                  30

Ser Val His Trp Val Arg Gln Pro Pro Gly Lys Gly Leu Glu Trp Leu
            35                  40                  45

Gly Thr Ile Trp Gly Gly Gly Ser Thr Asp Tyr Asn Ser Val Leu Lys
 50                  55                  60

Ser Arg Leu Ser Ile Ser Lys Asp Asn Ser Lys Ser Gln Val Leu Leu
 65                  70                  75                  80

Lys Val Asn Ser Leu Gln Thr Asp Asp Thr Ala Ile Tyr Tyr Cys Ala
                 85                  90                  95

Ser Gly Pro Tyr Tyr Tyr Thr Met Asp Tyr Trp Gly Gln Gly Thr Ser
            100                 105                 110

Val Thr Val Ser Ser
        115

<210> SEQ ID NO 5
<211> LENGTH: 345
<212> TYPE: DNA
<213> ORGANISM: Artificial Sequence
<220> FEATURE:
<221> NAME/KEY: CDS
<222> LOCATION: (1)..(342)
<220> FEATURE:
<223> OTHER INFORMATION: Description of Artificial Sequence: Synthetic
      construct

<400> SEQUENCE: 5 gct agc acc aag ggc cca tcg gtc ttc ccc ctg gca ccc tcc tcc aag         48
Ala Ser Thr Lys Gly Pro Ser Val Phe Pro Leu Ala Pro Ser Ser Lys
 1               5                  10                  15 agc acc tct ggg ggc aca gcg gcc ctg ggc tgc ctg gtc aag gac tac         96
Ser Thr Ser Gly Gly Thr Ala Ala Leu Gly Cys Leu Val Lys Asp Tyr
                 20                  25                  30 ttc ccc gaa ccg gtg acg gtg tcg tgg aac tca ggc gcc ctg acc agc        144
```

```
Phe Pro Glu Pro Val Thr Val Ser Trp Asn Ser Gly Ala Leu Thr Ser
             35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110 cca tgc taa                                                          345
Pro Cys <210> SEQ ID NO 6
<211> LENGTH: 114
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                      40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Cys

<210> SEQ ID NO 7
<211> LENGTH: 993
<212> TYPE: DNA
<213> ORGANISM: Homo sapiens
<220> FEATURE:
<221> NAME/KEY: CDS
<222> LOCATION: (1)..(990)

<400> SEQUENCE: 7 gct agc acc aag ggc cca tcg gtc ttc ccc ctg gca ccc tcc tcc aag       48
Ala Ser Thr Lys Gly Pro Ser Val Phe Pro Leu Ala Pro Ser Ser Lys
  1               5                  10                  15 agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
             20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
         35                      40                  45 ggc gtg cac acc ttc ccg gct gtc cta cag tcc tca gga ctc tac tcc      192
```

```
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acc cag acc          240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag          288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc          336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca          384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc          432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg          480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag          528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg          576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac          624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg          672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag          720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat          768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac          816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc          864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac          912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg          960
Val Phe Ser Cys Ser Val Met His Glu Ala Leu His Asn His Tyr Thr
305                 310                 315                 320 cag aag agc ctc tcc ctg tct ccg ggt aaa taa                              993
Gln Lys Ser Leu Ser Leu Ser Pro Gly Lys
                325                 330
```

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys

```
                1               5                  10                  15
              Ser Thr Ser Gly Gly Thr Ala Ala Leu Gly Cys Leu Val Lys Asp Tyr
                               20                  25                  30

Phe Pro Glu Pro Val Thr Val Ser Trp Asn Ser Gly Ala Leu Thr Ser
                               35                  40                  45

Gly Val His Thr Phe Pro Ala Val Leu Gln Ser Ser Gly Leu Tyr Ser
                               50                  55                  60

Leu Ser Ser Val Val Thr Val Pro Ser Ser Ser Leu Gly Thr Gln Thr
              65                  70                  75                  80

Tyr Ile Cys Asn Val Asn His Lys Pro Ser Asn Thr Lys Val Asp Lys
                               85                  90                  95

Lys Val Glu Pro Lys Ser Cys Asp Lys Thr His Thr Cys Pro Pro Cys
                              100                 105                 110

Pro Ala Pro Glu Leu Leu Gly Gly Pro Ser Val Phe Leu Phe Pro Pro
                              115                 120                 125

Lys Pro Lys Asp Thr Leu Met Ile Ser Arg Thr Pro Glu Val Thr Cys
                              130                 135                 140

Val Val Val Asp Val Ser His Glu Asp Pro Glu Val Lys Phe Asn Trp
              145                 150                 155                 160

Tyr Val Asp Gly Val Glu Val His Asn Ala Lys Thr Lys Pro Arg Glu
                              165                 170                 175

Glu Gln Tyr Asn Ser Thr Tyr Arg Val Val Ser Val Leu Thr Val Leu
                              180                 185                 190

His Gln Asp Trp Leu Asn Gly Lys Glu Tyr Lys Cys Lys Val Ser Asn
                              195                 200                 205

Lys Ala Leu Pro Ala Pro Ile Glu Lys Thr Ile Ser Lys Ala Lys Gly
                              210                 215                 220

Gln Pro Arg Glu Pro Gln Val Tyr Thr Leu Pro Pro Ser Arg Asp Glu
              225                 230                 235                 240

Leu Thr Lys Asn Gln Val Ser Leu Thr Cys Leu Val Lys Gly Phe Tyr
                              245                 250                 255

Pro Ser Asp Ile Ala Val Glu Trp Glu Ser Asn Gly Gln Pro Glu Asn
                              260                 265                 270

Asn Tyr Lys Thr Thr Pro Pro Val Leu Asp Ser Asp Gly Ser Phe Phe
                              275                 280                 285

Leu Tyr Ser Lys Leu Thr Val Asp Lys Ser Arg Trp Gln Gln Gly Asn
                              290                 295                 300

Val Phe Ser Cys Ser Val Met His Glu Ala Leu His Asn His Tyr Thr
              305                 310                 315                 320

Gln Lys Ser Leu Ser Leu Ser Pro Gly Lys
                              325                 330

<210> SEQ ID NO 9
<211> LENGTH: 984
<212> TYPE: DNA
<213> ORGANISM: Homo sapiens
<220> FEATURE:
<221> NAME/KEY: CDS
<222> LOCATION: (1)..(981)

<400> SEQUENCE: 9 gct agc acc aag ggc cca tcc gtc ttc ccc ctg gcg ccc tgc tcc agg        48
Ala Ser Thr Lys Gly Pro Ser Val Phe Pro Leu Ala Pro Cys Ser Arg
  1               5                  10                  15 agc acc tcc gag agc aca gcc gcc ctg ggc tgc ctg gtc aag gac tac        96
Ser Thr Ser Glu Ser Thr Ala Ala Leu Gly Cys Leu Val Lys Asp Tyr
                 20                  25                  30
```

```
ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acg aag acc      240
Leu Ser Ser Val Val Thr Val Pro Ser Ser Ser Leu Gly Thr Lys Thr
 65                  70                  75                  80 tac acc tgc aac gta gat cac aag ccc agc aac acc aag gtg gac aag      288
Tyr Thr Cys Asn Val Asp His Lys Pro Ser Asn Thr Lys Val Asp Lys
                 85                  90                  95 aga gtt gag tcc aaa tat ggt ccc cca tgc cca tca tgc cca gca cct      336
Arg Val Glu Ser Lys Tyr Gly Pro Pro Cys Pro Ser Cys Pro Ala Pro
            100                 105                 110 gag ttc ctg ggg gga cca tca gtc ttc ctg ttc ccc cca aaa ccc aag      384
Glu Phe Leu Gly Gly Pro Ser Val Phe Leu Phe Pro Pro Lys Pro Lys
        115                 120                 125 gac act ctc atg atc tcc cgg acc cct gag gtc acg tgc gtg gtg gtg      432
Asp Thr Leu Met Ile Ser Arg Thr Pro Glu Val Thr Cys Val Val Val
130                 135                 140 gac gtg agc cag gaa gac ccc gag gtc cag ttc aac tgg tac gtg gat      480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc      528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac      576
Asn Ser Thr Tyr Arg Val Val Ser Val Leu Thr Val Leu His Gln Asp
            180                 185                 190 tgg ctg aac ggc aag gag tac aag tgc aag gtc tcc aac aaa ggc ctc      624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga      672
Pro Ser Ser Ile Glu Lys Thr Ile Ser Lys Ala Lys Gly Gln Pro Arg
    210                 215                 220 gag cca cag gtg tac acc ctg ccc cca tcc cag gag gag atg acc aag      720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac      768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag      816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc      864
Thr Thr Pro Pro Val Leu Asp Ser Asp Gly Ser Phe Phe Leu Tyr Ser
        275                 280                 285 agg cta acc gtg gac aag agc agg tgg cag gag ggg aat gtc ttc tca      912
Arg Leu Thr Val Asp Lys Ser Arg Trp Gln Glu Gly Asn Val Phe Ser
    290                 295                 300 tgc tcc gtg atg cat gag gct ctg cac aac cac tac aca cag aag agc      960
Cys Ser Val Met His Glu Ala Leu His Asn His Tyr Thr Gln Lys Ser
305                 310                 315                 320 ctc tcc ctg tct ctg ggt aaa taa                                      984
Leu Ser Leu Ser Leu Gly Lys
                325

<210> SEQ ID NO 10
<211> LENGTH: 327
```

```
<212> TYPE: PRT
<213> ORGANISM: Homo sapiens

<400> SEQUENCE: 10

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
 65                 70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 11
<211> LENGTH: 321
<212> TYPE: DNA
<213> ORGANISM: Homo sapiens
<220> FEATURE:
<221> NAME/KEY: CDS
<222> LOCATION: (1)..(318)

<400> SEQUENCE: 11 acg gtg gct gca cca tct gtc ttc atc ttc ccg cca tct gat gag cag        48
```

```
Thr Val Ala Ala Pro Ser Val Phe Ile Phe Pro Ser Asp Glu Gln
 1               5                  10                  15 ttg aaa tct gga act gcc tct gtt gtg tgc ctg ctg aat aac ttc tat    96
Leu Lys Ser Gly Thr Ala Ser Val Val Cys Leu Leu Asn Asn Phe Tyr
             20                  25                  30 ccc aga gag gcc aaa gta cag tgg aag gtg gat aac gcc ctc caa tcg   144
Pro Arg Glu Ala Lys Val Gln Trp Lys Val Asp Asn Ala Leu Gln Ser
             35                  40                  45 ggt aac tcc cag gag agt gtc aca gag cag gac agc aag gac agc acc   192
Gly Asn Ser Gln Glu Ser Val Thr Glu Gln Asp Ser Lys Asp Ser Thr
 50                  55                  60 tac agc ctc agc agc acc ctg acg ctg agc aaa gca gac tac gag aaa   240
Tyr Ser Leu Ser Ser Thr Leu Thr Leu Ser Lys Ala Asp Tyr Glu Lys
 65                  70                  75                  80 cac aaa gtc tac gcc tgc gaa gtc acc cat cag ggc ctg agt tcg ccc   288
His Lys Val Tyr Ala Cys Glu Val Thr His Gln Gly Leu Ser Ser Pro
                 85                  90                  95 gtc aca aag agc ttc aac agg gga gag tgt taa                       321
Val Thr Lys Ser Phe Asn Arg Gly Glu Cys
                100                 105

<210> SEQ ID NO 12
<211> LENGTH: 106
<212> TYPE: PRT
<213> ORGANISM: Homo sapiens

<400> SEQUENCE: 12

Thr Val Ala Ala Pro Ser Val Phe Ile Phe Pro Ser Asp Glu Gln
 1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
             35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
                100                 105

<210> SEQ ID NO 13
<211> LENGTH: 66
<212> TYPE: DNA
<213> ORGANISM: Artificial Sequence
<220> FEATURE:
<221> NAME/KEY: CDS
<222> LOCATION: (1)..(66)
<220> FEATURE:
<223> OTHER INFORMATION: Description of Artificial Sequence: Synthetic
      polynucleotide

<400> SEQUENCE: 13 atg gac atg cgt gtg ccc gct caa ctc ctg ggc ctg ctg ctg ctc tgg    48
Met Asp Met Arg Val Pro Ala Gln Leu Leu Gly Leu Leu Leu Leu Trp
 1               5                  10                  15 ctc cca ggt gcg cgc tgt                                            66
Leu Pro Gly Ala Arg Cys
             20

<210> SEQ ID NO 14
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asp Met Arg Val Pro Ala Gln Leu Leu Gly Leu Leu Leu Leu Trp
 1               5                  10                  15

Leu Pro Gly Ala Arg Cys
            20

<210> SEQ ID NO 15
<211> LENGTH: 57
<212> TYPE: DNA
<213> ORGANISM: Artificial Sequence
<220> FEATURE:
<221> NAME/KEY: CDS
<222> LOCATION: (1)..(57)
<220> FEATURE:
<223> OTHER INFORMATION: Description of Artificial Sequence: Synthetic
      polynucleotide

<400> SEQUENCE: 15 atg gag ttc ggc ctg agc tgg ctg ttc ctg gtg gct att ctt aag ggt      48
Met Glu Phe Gly Leu Ser Trp Leu Phe Leu Val Ala Ile Leu Lys Gly
 1               5                  10                  15 gtc cag tgt                                                          57
Val Gln Cys <210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Glu Phe Gly Leu Ser Trp Leu Phe Leu Val Ala Ile Leu Lys Gly
 1               5                  10                  15

Val Gln Cys

<210> SEQ ID NO 17
<211> LENGTH: 1095
<212> TYPE: DNA
<213> ORGANISM: Mus musculus

<400> SEQUENCE: 17
gccaaaacaa cagccccatc ggtctatcca ctggcccctg tgtgtggaga tacaactggc      60
tcctcggtga ctctaggatg cctggtcaag ggttatttcc ctgagccagt gaccttgacc     120
tggaactctg gatccctgtc cagtggtgtg cacaccttcc cagctgtcct gcagtctgac     180
ctctacaccc tcagcagctc agtgactgta acctcgagca cctggcccag ccagtccatc     240
acctgcaatg tggcccaccc ggcaagcagc accaaggtgg acaagaaaat tgagcccaga     300
gggcccacaa tcaagccctg tcctccatgc aaatgcccag cacctaacct cttgggtgga     360
ccatccgtct tcatcttccc tccaaagatc aaggatgtac tcatgatctc cctgagcccc     420
atagtcacat gtgtggtggt ggatgtgagc gaggatgacc cagatgtcca gatcagctgg     480
tttgtgaaca acgtggaagt acacacagct cagacacaaa cccatagaga ggattacaac     540
agtactctcc gggtggtcag tgccctcccc atccagcacc aggactggat gagtggcaag     600
```

```
gagttcaaat gcaaggtcaa caacaaagac ctcccagcgc ccatcgagag aaccatctca    660
aaacccaaag ggtcagtaag agctccacag gtatatgtct tgcctccacc agaagaagag    720
atgactaaga aacaggtcac tctgacctgc atggtcacag acttcatgcc tgaagacatt    780
tacgtggagt ggaccaacaa cgggaaaaca gagctaaact acaagaacac tgaaccagtc    840
ctggactctg atggttctta cttcatgtac agcaagctga gagtggaaaa gaagaactgg    900
gtggaaagaa atagctactc ctgttcagtg gtccacgagg gtctgcacaa tcaccacacg    960
actaagagct ctcccggac tccgggtaaa tgagctcagc acccacaaaa ctctcaggtc   1020
caaagagaca cccacactca tctccatgct tcccttgtat aaataaagca cccagcaatg   1080
cctgggacca tgtaa                                                    1095

<210> SEQ ID NO 18
<211> LENGTH: 330
<212> TYPE: PRT
<213> ORGANISM: Mus musculus

<400> SEQUENCE: 18

Ala Lys Thr Thr Ala Pro Ser Val Tyr Pro Leu Ala Pro Val Cys Gly
 1               5                  10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285
```

```
Met Tyr Ser Lys Leu Arg Val Glu Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 19
<211> LENGTH: 15
<212> TYPE: DNA
<213> ORGANISM: Mus musculus

<400> SEQUENCE: 19
tcgagtgtaa ctttc                                             15

<210> SEQ ID NO 20
<211> LENGTH: 5
<212> TYPE: PRT
<213> ORGANISM: Mus musculus

<400> SEQUENCE: 20

Ser Ser Val Thr Phe
  1               5

<210> SEQ ID NO 21
<211> LENGTH: 9
<212> TYPE: DNA
<213> ORGANISM: Mus musculus

<400> SEQUENCE: 21 accacatcc                                                     9

<210> SEQ ID NO 22
<211> LENGTH: 3
<212> TYPE: PRT
<213> ORGANISM: Mus musculus

<400> SEQUENCE: 22

Thr Thr Ser
  1

<210> SEQ ID NO 23
<211> LENGTH: 24
<212> TYPE: DNA
<213> ORGANISM: Mus musculus

<400> SEQUENCE: 23
catcagtgga gtagttatcc cacg                                   24

<210> SEQ ID NO 24
<211> LENGTH: 8
<212> TYPE: PRT
<213> ORGANISM: Mus musculus

<400> SEQUENCE: 24

His Gln Trp Ser Ser Tyr Pro Thr
  1               5

<210> SEQ ID NO 25
<211> LENGTH: 33
<212> TYPE: DNA
<213> ORGANISM: Mus musculus

<400> SEQUENCE: 25
```

-continued gccagtggtc cttattacta tactatggac tac                           33

<210> SEQ ID NO 26
<211> LENGTH: 11
<212> TYPE: PRT
<213> ORGANISM: Mus musculus

<400> SEQUENCE: 26

Ala Ser Gly Pro Tyr Tyr Tyr Thr Met Asp Tyr
 1               5                  10

<210> SEQ ID NO 27
<211> LENGTH: 24
<212> TYPE: DNA
<213> ORGANISM: Mus musculus

<400> SEQUENCE: 27
atatggggtg gtggaagcac agac                                    24

<210> SEQ ID NO 28
<211> LENGTH: 8
<212> TYPE: PRT
<213> ORGANISM: Mus musculus

<400> SEQUENCE: 28

Ile Trp Gly Gly Gly Ser Thr Asp
 1               5

<210> SEQ ID NO 29
<211> LENGTH: 24
<212> TYPE: DNA
<213> ORGANISM: Mus musculus

<400> SEQUENCE: 29
gggttctcat tatccagata tagt                                    24

<210> SEQ ID NO 30
<211> LENGTH: 8
<212> TYPE: PRT
<213> ORGANISM: Mus musculus

<400> SEQUENCE: 30

Gly Phe Ser Leu Ser Arg Tyr Ser
 1               5

<210> SEQ ID NO 31
<211> LENGTH: 75
<212> TYPE: DNA
<213> ORGANISM: Mus musculus

<400> SEQUENCE: 31
caggtgcagc tgaaggagtc aggacctggc ctggtggcac cctcacagag cctgtccatc    60
acatgcactg tctct                                              75

<210> SEQ ID NO 32
<211> LENGTH: 25
<212> TYPE: PRT
<213> ORGANISM: Mus musculus

<400> SEQUENCE: 32

Gln Val Gln Leu Lys Glu Ser Gly Pro Gly Leu Val Ala Pro Ser Gln
 1               5                  10                  15

Ser Leu Ser Ile Thr Cys Thr Val Ser
                20                  25

<210> SEQ ID NO 33
<211> LENGTH: 51
<212> TYPE: DNA
<213> ORGANISM: Mus musculus

<400> SEQUENCE: 33
gtacactggg ttcgccagcc tccaggaaag ggtctggagt ggctgggaac g    51

<210> SEQ ID NO 34
<211> LENGTH: 17
<212> TYPE: PRT
<213> ORGANISM: Mus musculus

<400> SEQUENCE: 34

Val His Trp Val Arg Gln Pro Pro Gly Lys Gly Leu Glu Trp Leu Gly
 1               5                  10                  15

Thr

<210> SEQ ID NO 35
<211> LENGTH: 111
<212> TYPE: DNA
<213> ORGANISM: Mus musculus

<400> SEQUENCE: 35
tataactcag ttctcaaatc cagactgagc atcagcaagg acaactccaa gagccaagtt    60
ttgttaaaag tgaacagtct acaaactgat gacacagcca tatattactg t            111

<210> SEQ ID NO 36
<211> LENGTH: 37
<212> TYPE: PRT
<213> ORGANISM: Mus musculus

<400> SEQUENCE: 36

Tyr Asn Ser Val Leu Lys Ser Arg Leu Ser Ile Ser Lys Asp Asn Ser
 1               5                  10                  15

Lys Ser Gln Val Leu Leu Lys Val Asn Ser Leu Gln Thr Asp Asp Thr
            20                  25                  30

Ala Ile Tyr Tyr Cys
        35

<210> SEQ ID NO 37
<211> LENGTH: 33
<212> TYPE: DNA
<213> ORGANISM: Mus musculus

<400> SEQUENCE: 37
tggggtcaag gaacctcagt caccgtctcc tca    33

<210> SEQ ID NO 38
<211> LENGTH: 11
<212> TYPE: PRT
<213> ORGANISM: Mus musculus

<400> SEQUENCE: 38

Trp Gly Gln Gly Thr Ser Val Thr Val Ser Ser
 1               5                  10

<210> SEQ ID NO 39
<211> LENGTH: 78
<212> TYPE: DNA
<213> ORGANISM: Mus musculus -continued

<400> SEQUENCE: 39
caaattgttc tcacccagtc tccagcaatc ctgtctgcat ctctagggga ggagatcacc    60
ctaacctgca gtgccagc                                                 78

<210> SEQ ID NO 40
<211> LENGTH: 26
<212> TYPE: PRT
<213> ORGANISM: Mus musculus

<400> SEQUENCE: 40

Gln Ile Val Leu Thr Gln Ser Pro Ala Ile Leu Ser Ala Ser Leu Gly
 1               5                  10                  15
Glu Glu Ile Thr Leu Thr Cys Ser Ala Ser
            20                  25

<210> SEQ ID NO 41
<211> LENGTH: 51
<212> TYPE: DNA
<213> ORGANISM: Mus musculus

<400> SEQUENCE: 41
atgcactggt accagcagaa gtcaggcact tctcccaaac tcttgattta t              51

<210> SEQ ID NO 42
<211> LENGTH: 17
<212> TYPE: PRT
<213> ORGANISM: Mus musculus

<400> SEQUENCE: 42

Met His Trp Tyr Gln Gln Lys Ser Gly Thr Ser Pro Lys Leu Leu Ile
 1               5                  10                  15
Tyr

<210> SEQ ID NO 43
<211> LENGTH: 108
<212> TYPE: DNA
<213> ORGANISM: Mus musculus

<400> SEQUENCE: 43
aacctggctt ctggagtccc ttctcgcttc agtggcagtg ggtctgggac cttttattct    60
ctcacaatca gcagtgtgga ggctgaagat gctgccgatt attactgc                108

<210> SEQ ID NO 44
<211> LENGTH: 36
<212> TYPE: PRT
<213> ORGANISM: Mus musculus

<400> SEQUENCE: 44

Asn Leu Ala Ser Gly Val Pro Ser Arg Phe Ser Gly Ser Gly Ser Gly
 1               5                  10                  15
Thr Phe Tyr Ser Leu Thr Ile Ser Ser Val Glu Ala Glu Asp Ala Ala
            20                  25                  30
Asp Tyr Tyr Cys
        35

<210> SEQ ID NO 45
<211> LENGTH: 33
<212> TYPE: DNA
<213> ORGANISM: Mus musculus

<400> SEQUENCE: 45
ttcggctcgg ggacaaagtt ggaaataaaa cgg                                33

<210> SEQ ID NO 46
<211> LENGTH: 11
<212> TYPE: PRT
<213> ORGANISM: Mus musculus

<400> SEQUENCE: 46

Phe Gly Ser Gly Thr Lys Leu Glu Ile Lys Arg
 1               5                  10

<210> SEQ ID NO 47
<211> LENGTH: 124
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(26)
<223> OTHER INFORMATION: region may encompass 25-26 variable amino acids
<220> FEATURE:
<221> NAME/KEY: MOD_RES
<222> LOCATION: (35)..(53)
<223> OTHER INFORMATION: region may encompass 15-19 variable amino acids
<220> FEATURE:
<221> NAME/KEY: MOD_RES
<222> LOCATION: (62)..(101)
<223> OTHER INFORMATION: region may encompass 35-40 variable amino acids
<220> FEATURE:
<221> NAME/KEY: MOD_RES
<222> LOCATION: (113)..(124)
<223> OTHER INFORMATION: region may encompass 10-12 variable amino acids
<220> FEATURE:
<223> OTHER INFORMATION: see specification as filed for detailed
      description of preferred embodiments

<400> SEQUENCE: 47

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Gly Phe Ser Leu Ser Arg
             20                  25                  30

Tyr Ser Xaa Xaa Xaa Xaa Xaa Xaa Xaa Xaa Xaa Xaa Xaa Xaa Xaa Xaa
         35                  40                  45

Xaa Xaa Xaa Xaa Xaa Ile Trp Gly Gly Gly Ser Thr Asp Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Ala Ser Gly Pro Tyr Tyr Tyr Thr Met Asp Tyr
            100                 105                 110

Xaa Xaa Xaa Xaa Xaa Xaa Xaa Xaa Xaa Xaa Xaa Xaa
        115                 120

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(26)
<223> OTHER INFORMATION: region may encompass 25-26 variable amino acids
<220> FEATURE:

```
<221> NAME/KEY: MOD_RES
<222> LOCATION: (32)..(50)
<223> OTHER INFORMATION: region may encompass 15-19 variable amino acids
<220> FEATURE:
<221> NAME/KEY: MOD_RES
<222> LOCATION: (54)..(93)
<223> OTHER INFORMATION: region may encompass 35-40 variable amino acids
<220> FEATURE:
<221> NAME/KEY: MOD_RES
<222> LOCATION: (102)..(113)
<223> OTHER INFORMATION: region may encompass 10-12 variable amino acids
<220> FEATURE:
<223> OTHER INFORMATION: see specification as filed for detailed
      description of preferred embodiments

<400> SEQUENCE: 48

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Ser Ser Val Thr Phe Xaa
                20                  25                  30

Xaa Xaa Xaa Xaa Xaa Xaa Xaa Xaa Xaa Xaa Xaa Xaa Xaa Xaa
            35                  40                  45

Xaa Xaa Thr Thr Ser Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa His Gln Trp
                85                  90                  95

Ser Ser Tyr Pro Thr Xaa Xaa Xaa Xaa Xaa Xaa Xaa Xaa Xaa Xaa
                100                 105                 110

Xaa
```

NUCLEOTIDE AND PROTEIN SEQUENCES OF AN ANTIBODY DIRECTED AGAINST AN EPITOPE COMMON TO HUMAN ACIDIC AND BASIC FERRITINS, MONOCLONAL ANTIBODIES OR ANTIBODY-LIKE MOLECULES COMPRISING THESE SEQUENCES AND USES THEREOF

FIELD OF THE INVENTION

The present invention relates to chimeric and humanized monoclonal antibodies, fragments thereof and antibody-like molecules that recognize an epitope common to human acidic and basic isoferritins. These chimeric and humanized anti-ferritin monoclonal antibodies, fragments thereof and antibody-like molecules can be used in pharmaceutical compositions for therapy to target various cancer cells in a mammal. A method for delivering anti-ferritin monoclonal antibodies, fragments thereof and antibody-like molecules to cancerous lymph cells, pancreatic cells, lymphatic endothelium cells, and liver cells is also disclosed, as well as methods for treating pancreatic cancer, hepatocellular carcinomas, Kaposi's sarcoma and Hodgkin's lymphoma.

BACKGROUND OF THE INVENTION

It is well known that the immune system plays a role in cancer progression. Immunotherapy is a fairly new but promising weapon in the arsenal of anticancer treatments. Cancer immunotherapy aims at enhancing the body's natural ability to defend itself against malignant tumors through stimulation of the patient immune system via various pharmacological agents such as vaccines, T cell infusions, cytokine infusions or antibodies. These pharmaceutical agents can act by stimulating an antitumor response by increasing the number of effector cells, by producing lymphokines, by decreasing suppressor mechanisms, by improving tolerance to cytotoxic drugs or chemotherapy and/or by altering tumor cells to increase their immunogenicity.

Monoclonal antibodies can act either indirectly by recruiting cells, which is know as antibody-dependent cell mediated cytotoxicity (ADCC), or by triggering directly cell death, which is known as complement dependent toxicity (CDC).

An example of antibody-dependent cell mediated toxicity (ADCC) is that induced by rituximab, a chimeric antibody that targets the CD20 antigen, expressed on a significant number of B cell malignancies. The constant part (Fc) of the antibody binds to the Fc receptors found on monocytes, macrophages and natural killer cells, which leads to destruction of the tumor cells. The monocytes, macrophages and natural killer cells can in turn engulf the bound tumor cells and destroy it. Natural killer cells also secrete cytokines that then is leads to cell death.

In complement dependent cytotoxicity (CDC), the monoclonal antibody binds to its receptor on the tumor cells and initiates the complement system, which causes cell membrane permeation leading inevitably to cell death.

In yet another scenario, monoclonal antibodies can kill cells by blocking growth mechanisms or by triggering apoptosis.

Hence, antibodies can act by different ways to treat cancer. Moreover, they can either be used alone as described above or they can be coupled to toxins, cytotoxic agents, drugs, immune killer cells or radioisotopes to deliver a cytotoxic substance or compound at the tumor sites. Examples of radioisotopes that can be used in radioimmunotherapy include alpha- or beta-emitting radioisotopes. An example of a toxin conjugated to an antibody for use in antibody therapy is pseudomonas exotoxin. Examples of drugs that can be used include alkylating agents, platinum drugs, pyrimidine drugs and the like.

However, one of the problems encountered using antibody therapy is that antibodies can target cells expressing an antigen that can be present in both normal and cancerous cells and thus there is a possibility of reacting with normal cells or tissues. Cross reactivity with normal tissues or normal cells can lead to detrimental results. Therefore, tumor specific antigens or antigens overexpressed in tumor cells are generally looked for.

Although murine monoclonal antibodies are easily produced and generally functional, they are recognized as foreign antigens by a human host and human anti-mouse antigens (HAMA) are produced. Because repeated administration of murine antibodies is required, such administration can cause systemic inflammatory effects. To overcome the problems with using murine monoclonal antibodies, one can generate human antibodies directly from humans. However, this process causes ethical problems since one cannot challenge humans with antigens in order to produce antibodies. Furthermore, it is not easy to generate human antibodies against human tissue. Thus, the use of chimeric or humanized antibodies is preferred since they elicit less of a human anti-mouse antibody response.

Chimeric antibodies are antibodies which have variable regions from one species and constant regions from another species. Examples of chimeric antibodies are described in WO88/04936. However, generation of humanized antibodies by introducing human sequences is very difficult and unpredictable. This is due to the significant loss of binding affinity from the grafting of the hypervariable regions and the distortion of the complementary-determining region (CDR) conformation by the human framework. Furthermore, although chimeric antibodies can be generated in vitro, functional assays such as CDC assays and ADCC assays cannot inherently predict the in vivo capability of a chimeric antibody to destroy or deplete target cells expressing a specific antigen. Thus in many instances, it is not predictable whether a chimeric or humanized antibody can indeed function properly for antibody therapy.

Ferritin is an iron storage protein having a molecular weight of 440,000. It is over expressed in some tumors such as breast cancer (Guner et al., "Cytosol and serum ferritin in breast carcinoma." *Cancer Lett,* 67(2-3):103-112 (1992); Weinstein et al., "Tissue ferritin concentration and prognosis in carcinoma of the breast." *Breast Cancer Res Treat;* 14 (3):349-53 (1989)), Hodgkin's lymphoma (Eshhar et al., "Ferritin, a Hodkin;s disease Associated Antigen." is PNAS U.S.A.; 71 (10):3956-60 (1974)) and pancreatic cancer (Drysdale et al., "Human isoferritins in normal and disease states." *Semin Hematol,* 14 (1):71-88 (1977) Marcus et al., "Isolation of ferritin from human mammary and pancreatic carcinomas by means of antibody immunoadsorbents." *Arch Biochem Biophys,* 162 (2):493-501 (1974)).

A radiolabelled polyclonal antiferritin serum obtained by immunization of rabbits with ferritin isolated from the spleen of a Hodgkin's disease patient showed antitumoral activity in patients with Hodgkin's disease (Vriesendorp et al., "Radiolabelled immunoglobulin therapy in patients with Hodgkin's disease." *Cancer Biother Radiopharm;* 15 (5):431-45 (2000). However, polyclonal antibodies have several drawbacks in comparison to monoclonal antibodies such as the limited batch size. Indeed, Vriesendorp and colleagues noticed differences in response rates in two trials on Hodgkin's lymphoma patients when they used two different batches of the polyclonal antiferritin antibody (Vriesendorp et al., "Review of five consecutive studies of radiolabeled immunoglobulin therapy in Hodgkin's disease." *Cancer Res,* 55 (23 Suppl): 5888s-92s (1995). Thus, monoclonal antibodies are preferable to use in therapeutic applications in lieu of polyclonal antibodies for many reasons.

U.S. Pat. No. 7,153,506 describes the use of murine anti-ferritin monoclonal antibodies to treat some forms of cancer. However, as set forth above there are problems associated with treating humans with murine monoclonal antibodies (such as HAMA production).

Pancreatic cancer has a very poor prognosis with less than a 5% survival rate at five years. Neither external beam radiation nor chemotherapy, alone or in combination have given encouraging results so far. Up to 95% of the cases of pancreatic cancer arise from the exocrine part of the pancreas, which is that part of the pancreas which produces enzymes in acinar cells. Most pancreatic cancer is found in the ductal cells. Therefore, the term adenocarcinoma (duct-like) has been assigned to the most common cause of pancreatic cancers. More than 60,000 Europeans are diagnosed with adenocarcinoma each year. The survival period from the time of diagnosis until the time of death is the worst for any cancers and is generally about 3½ to 6 months. Surgical removal of the tumor is an option, but only about 15% to 20% of patients with pancreatic cancer are eligible for surgery.

Besides pancreatic cancer, other cancers such as Hodgkins lymphoma, breast cancer and hepatocellular carcinomas are also cancers that have high death rates and, for some of them, limited opportunities for surgical removal. For instance in hepatocellular carcinoma if the tumor is less than 5 cm, exists on a sole lobe in the liver and there is no invasion of liver vasculature by the carcinoma, the tumor can be removed surgically. However, surgical removal is impossible in many cases due to the non-diagnosed progression of the disease.

There is a need for a method of treating the above quoted cancers that does not involved surgical intervention and that would reduce the secondary effects associated with chemotherapy.

It is thus object of the present invention to provide pharmaceutical compositions containing a chimeric or humanized anti-ferritin antibody or fragments thereof as well as antibody-like molecules that can bind human acidic and basic ferritin for treating certain cancers.

It is another object of the present invention to provide pharmaceutical compositions containing a chimeric or humanized anti-ferritin antibody or fragments thereof as well as antibody-like molecules that can treat pancreatic cancer, breast cancer, hepatocellular carcinomas, Kaposi's sarcoma and Hodgkin's lymphoma.

It is yet another object of the present invention to provide chimeric or humanized monoclonal antibodies which are specific to human acidic and basic ferritin.

It is another object of the present invention to provide chimeric or humanized antibodies specific to human acidic and basic ferritin that bind to human ferritin.

Yet another object of the present invention provides methods of treating cancers selected from the group of pancreatic cancer, breast cancer, hepatocellular carcinomas, Kaposi's sarcoma and Hodgkin's lymphoma by administering a chimeric or humanized anti-ferritin antibody or fragments thereof as well as antibody-like molecules.

Another object of the present invention provides methods of treating cancers selected from the group of pancreatic cancer, breast cancer, hepatocellular carcinomas, Kaposi's sarcoma and Hodgkin's lymphoma by administering a radio-labelled chimeric or humanized anti-ferritin antibody or fragments thereof as well as antibody-like molecules conjugated to a chelator.

Another object of the present invention is to provide a method for delivering humanized or chimeric anti-ferritin antibodies to cancerous lymph cells, pancreatic cells, lymphatic endothelium cells, and liver cells.

Yet another object of the present invention is the use of a chimeric or humanized anti-ferritin antibody or fragments thereof as well as antibody-like molecules for the preparation of a drug to treat certain cancers such as pancreatic cancer, breast cancer, hepatocellular carcinomas, Kaposi's sarcoma and Hodgkin's lymphoma.

Yet another object of the present invention is the provision of nucleic acid sequences that can be placed in vectors to produce all or part of a chimeric or humanized anti-ferritin antibody or fragments thereof as well as antibody-like molecules of the present invention via the production in cells.

These and other objects of the present invention will become apparent from the following description, examples or preferred embodiments.

SUMMARY OF THE INVENTION

In one aspect, the present invention concerns a, single chain, polypeptide comprising, from N-terminal to C terminal, SEQ ID NO:30, SEQ ID NO:28 and SEQ ID NO:26 (to form a VH domain). In another aspect, this polypeptide also comprises, in the C-terminal of SEQ ID NO:26, a CH1 domain such as SEQ ID NO:6, as well as a Fc region such as SEQ ID NO:8, SEQ ID NO:10 or SEQ ID NO:18, to form a heavy chain. In another aspect, the present invention is directed to a single chain polypeptide comprising, from N-terminal to C terminal, SEQ ID NO:20, SEQ ID NO:22 and SEQ ID NO:24, to form a VL domain. In another aspect, this single polypeptide also comprises, in the C-terminal of SEQ ID NO:24, a kappa or a lambda chain such as SEQ ID NO:12 to form a light chain.

In another aspect, the invention concerns a molecule, optionally binding both human acidic and basic ferritin, comprising a light chain as defined herein, a heavy chain as defined herein or any combination thereof. In a yet another aspect, said molecule is a chimeric anti-ferritin monoclonal antibody that binds both human acidic and basic ferritin. In a yet another aspect, the chimeric anti-ferritin monoclonal antibody comprises the sequences of SEQ ID Nos. 2, 4, 6, 8 and 12, or SEQ ID Nos.:2, 4, 6, 10 and 12.

In another aspect the invention concerns a chimeric monoclonal anti-ferritin antibody that binds both human acidic and basic ferritin comprising the amino acid sequences of SEQ ID Nos. 2, 4, 6, 12 and 18.

A pharmaceutical composition comprising a molecule according to the definition given herein, especially a chimeric or humanized monoclonal anti-ferritin antibody that binds both human acidic and basic ferritin, fragment thereof or antibody-like molecules of the invention that binds both human acidic and basic ferritin as disclosed herein, and especially a chimeric anti-ferritin monoclonal antibody comprising the amino acid sequences of SEQ ID Nos. 2, 4, 6, 8 and 12 or SEQ ID Nos. 2, 4, 6, 10 and 12, said composition comprising further a pharmaceutically acceptable vehicle and optionally a pyrimidine drug, is yet another aspect of the invention.

In yet another aspect a method of delivering a drug, radioactive materials, toxins, immune killer cells or combinations thereof to cells containing basic and acidic ferritin, said method comprising administering a composition comprising a heavy chain, a light chain, any combination thereof, a chimeric or humanized antibody or a fragment thereof or an antibody-like molecule of the invention, and a composition selected from the group of a drug, radioactive materials, toxins, immune killer cells and combinations thereof wherein said composition is in a pharmaceutically acceptable carrier is provided.

A method of treating a cancer selected from the group of pancreatic cancer, Hodgkin's lymphoma, Kaposi's sarcoma and hepatocellular carcinoma said method comprising administering to a mammal in need of such treatment a composition comprising a heavy chain, a light chain, any combination thereof, a chimeric or humanized antibody, a fragment thereof or an antibody-like molecule of the invention, especially a molecule comprising SEQ ID Nos: 2, 4, 6, 8 and 12 or SEQ ID Nos. 2, 4, 6, 10 and 12, and optionally a composition selected from the group of a drug, radioactive isotopes, toxins, immune killer cells and combinations thereof wherein said composition is in a pharmaceutically acceptable carrier is yet another aspect of the present invention.

A nucleic acid sequence comprising SEQ ID Nos: 1 and 11 or a nucleic acid comprising SEQ ID Nos. 3, 5 and 7 or SEQ ID Nos 3, 5 and 9 or SEQ ID Nos 3, 5 and 17, or a nucleic acid sequence comprising SEQ ID NOs. 1, 3, 5, 7 and 11 or SEQ ID Nos 1, 3, 5, 9 and 11, or a nucleic acid comprising SEQ ID Nos: 1, 11, 13 or a nucleic acid comprising SEQ ID Nos 3, 5, 7 and 15, or a nucleic acid comprising SEQ ID Nos. 3, 5, 9 and 15 or a nucleic acid comprising SEQ ID Nos. 3, 5, 15 and 17, as well as vectors containing at least one of these nucleic acid sequences and cells transformed with at least one of these vectors are also described. A nucleic acid comprising SEQ ID NO:19, 21 and 23 and optionally SEQ ID NO:11 as well as a nucleic acid comprising SEQ ID NO:29, 27 and 25 and optionally SEQ ID NO:5, and further optionally SEQ ID NO:7, NO:9 or NO:17 are also part of the invention.

BRIEF DESCRIPTION OF THE DRAWINGS

FIG. 1 is the VL nucleic acid (SEQ ID NO: 1) and amino acid sequence (SEQ ID NO:2) from clone AMB8LK. The VL domain is composed of the FR1 region (amino acids 1-26), the CDR1 region (amino acids 27-31), the FR2 region (amino acids 32-48), the CDR2 region (amino acids 49-51), the FR3 region (amino acids 52-87), the CDR3 region (amino acids 88-95) and the FR4/J region (amino acids 96-106).

FIG. 2 is the VH nucleic acid (SEQ ID NO: 3) and amino acid sequence (SEQ ID NO:4) from clone AMB8LK. The VH domain is composed of the FR1 region (amino acids 1-25), the CDR1 region (amino acids 26-33), the FR2 region (amino acids 34-50), the CDR2 region (amino acids 51-58), the FR3 region (amino acids 59-95), the CDR3 region (amino acids 96-106) and the FR4/J region (amino acids 107-117).

FIG. 3 is the CH1 nucleic acid (SEQ ID NO: 5) for the Fab'2-3 cyst construct and amino acid sequence (SEQ ID NO:6) for the Fab'2-3 cyst construct. The CH1 was cloned from a human constant gamma 1 nucleic acid sequence, supplemented by an additional cysteine and a stop codon.

FIG. 4 is the nucleic acid sequence of the human gamma 1 constant region (SEQ ID NO: 7) and the amino acid sequence of the human gamma 1 constant region (SEQ ID No; 8) (Genbank accession number BC073782). The second TCC codon was modified to A&C (underlined) to create a NheI cloning site.

FIG. 5 is the nucleic acid sequence of the human gamma 4 constant region (SEQ ID NO: 9) and the amino acid sequence of the human gamma 4 constant region (SEQ ID No: 10) (Genbank accession number BC025985). The second TCC codon was modified to AGC (underlined) to create a NheI cloning site.

FIG. 6 is the nucleic acid sequence of the human kappa constant region (SEQ ID NO: 11) and the amino acid sequence of the human kappa constant region (SEQ ID No: 12).

FIG. 7 is the nucleic acid sequence of the human VL signal peptide sequence (SEQ ID NO: 13) and the amino acid sequence of the human VL signal peptide sequence (SEQ ID NO: 14).

FIG. 8 is the nucleic acid sequence of the human VH signal peptide sequence (SEQ ID NO: 15) and the amino acid sequence of the human VH signal peptide sequence (SEQ ID NO: 16).

FIG. 9A is the nucleic acid sequence of the constant region from murine γ 2a (SEQ ID NO: 17)

FIG. 9B is the amino acid sequence of the constant region from murine γ 2a (SEQ ID NO: 18).

FIG. 10 is the chemical structure of the chelates used in the examples. A: pSCN-Bz-DTPA: 2-(4-isothiocyanatobenzyl)-diethylenetriaminepentaacetic acid. B: pSCN-Bz-CHX-A"-DTPA: (R)-2-amino-3-(4-isothiocyanatophenyl)propyl]-trans-(S,S)-cyclohexane-1,2-diamine-pentaacetic acid: C: pSCN-Bz-DOTA: 2-(4,isothiocyanatobenzyl)-1,4,7,10-tetraazacyclodedecane-1,4,7,10-tetraacetic acid.

BRIEF DESCRIPTION OF THE SEQUENCES

Figure 11:
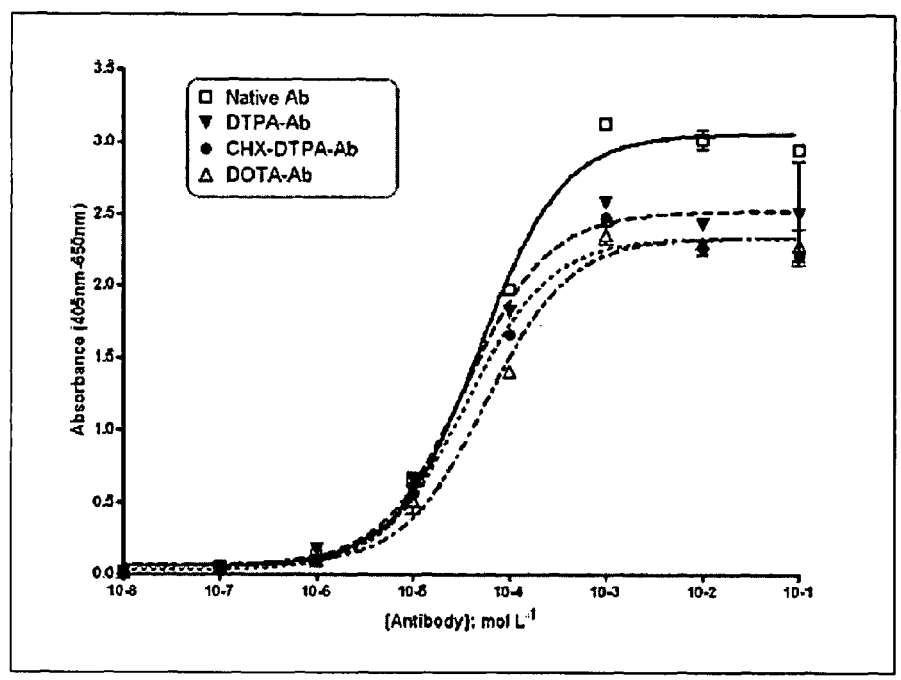
FIG. 11 is a graph showing the immunoreactivity of the cold conjugated antibody by ELISA. After conjugation of about 3 chelates per antibody the assessment of the immunoreactivity of the immunoconjugates was performed by ELISA. Pure ferritin was immobilized at 5 µg/ml in PBS, then incubated with various concentrations of the immunoconjugates. The control was the unconjugated AMB8LK.

Sequences (SEQ ID) used in the present application are the following:

| Name | Nucleotide SEQ ID | Protein SEQ ID |
|---|---|---|
| VL domain from clone AMB8LK | 1 | 2 |
| VH domain from clone AMB8LK | 3 | 4 |
| CH1 domain (Fab'2-3 cyst construct) | 5 | 6 |
| human gamma 1 constant region | 7 | 8 |
| human gamma 4 constant region | 9 | 10 |
| human kappa constant region | 11 | 12 |
| VL signal peptide | 13 | 14 |
| VH signal peptide | 15 | 16 |
| constant region from murine γ 2a | 17 | 18 |
| VL domain CDR1 | 19 | 20 |
| VL domain CDR2 | 21 | 22 |
| VL domain CDR3 | 23 | 24 |
| VH domain CDR3 | 25 | 26 |
| VH domain CDR2 | 27 | 28 |
| VH domain CDR1 | 29 | 30 |
| VH domain FR1 | 31 | 32 |
| VH domain FR2 | 33 | 34 |
| VH domain FR3 | 35 | 36 |
| VH domain FR4 | 37 | 38 |
| VL domain FR1 | 39 | 40 |
| VL domain FR2 | 41 | 42 |
| VL domain FR3 | 43 | 44 |
| VL domain FR4 | 45 | 46 |

DESCRIPTION OF THE PREFERRED EMBODIMENTS OF THE INVENTION

As used herein the term "consisting essentially of" when used in connection with nucleic acids or amino acids means that other minor ingredients or molecules may be present with the amino acid or nucleic acid sequences. The nucleic acid sequence has the exact same length as indicated in the sequence identification number, but may have 3 to 12 extra or less nucleotides at the N- and C-terminals. Likewise, the amino acid sequence has the exact same length as indicated in the sequence identification number but from 1 to 4 extra or less amino acids may be added or deleted at the N- or C-terminals. These extra or deleted amino acids do not modify the binding and/or the activity of the chimeric monoclonal antibody to ferritin.

As used herein the term "chelating agent" means any chemical substance that complexes with a metal to form a chelate. Chelating agents are organic compounds that are capable of forming coordinate or ionic bonds with metals through two or more atoms of the organic compound.

The term "mammal" encompasses any of various warm-blooded vertebrate animals of the class Mammalia, including humans, characterized by a covering of hair on the skin and, in the female, milk-producing mammary glands for nourishing the young. In a particular embodiment, the invention is directed to a non-human mammal.

The term "chimeric antibody" and "humanized antibody" refer to an antibody whose regions are derived from two different species, generally murine and human. The term "chimeric antibody" is specifically used to refer to a variable region (composed of a VL and VH and responsible for the binding of the antigen) of a first species, such as a mouse with the constant region of a second species, such as human. The expression "humanized antibody" refers rather to the grafting of complementary determining-regions (CDR) from a first species, such as mouse, into human framework regions (FR).

The term "monoclonal antibody" refers to an antigen-binding protein having four-polypeptide chains consisting of two heavy and two light chains. The chains, that are stabilized by interchain disulfide bonds, have the ability to specifically bind antigen. Both heavy and light chains are folded into domains, which is the globular region of the heavy or light chain containing peptide loops. The domains are either "constant" or "variable" depending upon the amount of variation in the sequence. Constant domains on the light chain are referred to as light chain constant regions or CL. Constant domains on the heavy chain are referred to as heavy chain constant domains or CH. Variable domains on the light chain are referred to as light chain variable regions or VL domain, while heavy domains on the variable chains are referred to as heavy chain variable regions or VH domain. Each variable domain (VH or VL) consists of CDR (complementary determining region) and FR (framework region), that are alternatively linked together i.e., from N-terminal to C-terminal: FR1-CDR1-FR2-CDR2-FR3-CDR3-FR4.

The expression "monoclonal antibody" encompasses:
(1) monospecific antibodies i.e., molecules wherein the two antigen binding sites (domains formed by the interaction of the VH and VL regions as defined herein, and interacting with the antigen) recognize and bind the same antigen (e.g., an antigen common to human acidic and basic ferritins). In this aspect, the two heavy chains and two light chains as defined herein (or at least the two VH and two VL as defined herein) have the same amino acid sequence;
(2) trifunctional antibodies i.e., bispecific molecules as disclosed hereinafter and further having an Fc region (CH2 and CH3 domains) of any origin, particularly of human origin.

The term "antibody-like molecule" refers to a molecule having all or part of the variable heavy and light domains of the AMB8LK antibody, and not having the conventional structure of a four-chain antibody, but conserving the capacity to interact and bind with the antigen (ferritin). In a particular embodiment, the antibody-like molecules of the invention comprise the CDR1, CDR2 and CDR3 regions of the VL and/or VH domains of the AMB8LK antibody. This encompasses:
(1) scFv, i.e., a VH domain as defined herein genetically associated (optionally via a linker) to a VL domain as defined herein, as well as molecules comprising at least one scFv, such as Bis ScFv molecules (two ScFv having same or different antigen binding linked together (optionally via a linker));
(2) diabody molecules i.e., the heavy chain variable domain derived from a first antibody (a first VH domain (VH1) such as one defined herein) connected to the light chain variable domain derived from a second antibody (VL2) on the same polypeptide chain (VH1-VL2) connected by a peptide linker that is too short to allow pairing between the two domains on the same chain, interacting with the heavy chain variable domain of derived from a second antibody (VH2) connected to the light chain variable domain derived from a first antibody (a first VL domain (VL1) such as one defined herein) on the same polypeptide chain (VH2-VL1), wherein VL1 and VH1 form a first antigen-binding site (recognizing and/or binding an antigen common to human acidic and basic ferritin) and VL2 and VH2 form a second antigen binding site (recognizing and/or binding a similar or a different antigen and/or epitope from the first binding antigen binding site);

(3) bispecific molecules i.e., that the two antigen binding sites of a Fab$_2$ fragment (variable and CH1 domains of light and heavy chains) interact with different antigens (or epitopes). In this aspect, the two heavy chains (or the two VH domains) have a different amino acid sequence, and/or the two light chains (or the two VL domains) have a different amino acid sequence. In a bi-specific molecules of the invention, at least one of the two antigen binding sites is a ferritin binding site consisting of a VL or VH domains as defined herein, such as respectively SEQ ID NO:2 and SEQ ID NO:4 or variants thereof;

(4) trispecific molecules i.e., that the two antigen binding sites of a Fab$_3$ fragment (variable and CH1 domains of light and heavy chains) interact with different antigens (or epitopes). In this aspect, the three heavy chains (or at the three VH domains) have a different amino acid sequence, and/or the three light chains (or the three VL domains) have a different amino acid sequence. In a tri-specific molecules of the invention, at least one of the three antigen binding sites is a ferritin binding site consisting of a VL or VH domains as defined herein, such as respectively SEQ ID NO:2 and SEQ ID NO:4 or variants thereof;

(5) V$_{HH}$ (VH domain devoid of light chain) i.e., a VH domain as defined herein which has the capacity to interact as such with the antigen, without the presence of a variable light domain (VL). These V$_{HH}$ can be obtained by recombinant techniques or by purification from animal of the camelid family or from sharks.

By "constant region" is meant the CH1, CH2 and CH3 domains (CH2 and CH3 forming the Fc region). In the monoclonal antibodies of the present invention, the murine constant CH1 domain and murine constant CH2 and CH3 domains are replaced, independently from one another, with human constant CH1 and human constant CH2 and CH3 regions. Therefore, in one embodiment, the CH2 and CH3 domains (Fc region) of a murine monoclonal antibody are replaced by a CH2 and CH3 regions of human origin. The human Fc region may be a mu, gamma, alpha, delta or epsilon chain, optionally derived from human immunoglobulins. In a particular embodiment, the human Fc region is selected from IgG1 and IgG4. In another embodiment, the CH1 domain of a monoclonal antibody is replaced by a human CH1 region, such as kappa or lambda chains, optionally derived from human immunoglobulins.

By "functional fragment" is meant a monoclonal antibody fragment, which retains its binding properties to specifically bind to both human acidic and basic ferritin. In another aspect "functional fragment" encompasses a monoclonal antibody that exhibits the same or substantially the same binding affinity and avidity as the non-fragmented chimeric anti-ferritin monoclonal antibody or parent monoclonal antibody. The binding affinity of the monoclonal antibody functional fragment should not be less than 10% of the parent antibody. In another aspect the binding affinity of the monoclonal antibody fragment should not be less than 25% of the parent antibody. In another aspect binding affinity of the monoclonal antibody fragment should not be less than 30% or not be less than 50% of the parent antibody. Methods for measuring binding affinity are well known in the art and include, for example competition assays, Scatchard analysis and half-maximal binding assays.

By the term "variant" when referring to the sequence variants means sequences having a degree of similarity of at least 90%, 95% or 98% similarity with SEQ ID Nos: 2, 4, 6, 8, 10, 12, 16, 18, 20, 22, 24, 26, 28, 30, 32, 34, 36, 38, 40, 42, 44 and 46, using sensitive and rapid sequence comparison programs such as BLAST, FASTA, GAP, BESTFIT, clustalW or any other relevant program.

Clearly, the amino acid sequences with a specific identity defined above have a majority of conservative amino acid substitutions. Conservative amino acid substitutions include amino acid substitutions of the same class. These classes comprise, for example, amino acids having uncharged polar side chains, such as Asn, Gln, Ser, Thr or Tyr; amino acids containing basic side chains, such as His, Lys or Arg; amino acids containing acidic side chains, such as Glu or Asp and amino acids containing non-polar side chains, such as Ala, Gly, Leu, Val, Ile, Phe, Cys or Trp.

For example, with respect to FIG. 4, the Asn at amino acid position 42 can be substituted with Gln, Ser, Thr or Tyr; the Lys at amino acid position 11 can be modified to His or Arg; the Ala at amino acid position 7 can be replaced by Gly, Leu, Val, Ile, Phe, Cys or Trp. Likewise, conservative substitutions can be made to any of the amino acids sequences of the present invention in the same manner. It will be appreciated that the person skilled in the art would ensure that once these substitutions are made to the protein sequence or sequences, human ferritin binding activity is retained. This can be accomplished by using the RIA and ELISA assays described in the examples.

The term "epitope" refers to the site of the antigen to which the antibody specifically binds. An epitope has at least 3 to 15 amino acids in a unique conformation (linear or conformational epitope). X-ray crystallography, 2-dimensional nuclear magnetic resonance or epitope mapping can be used as methods for determining spatial conformation of epitopes.

Antibodies that recognize the same epitope can be identified by a competitive binding assay, which is known in the art. Examples of competitive binding assays include RIA and ELISA.

The term "effective dosage" or "effective dose" means the amount sufficient to achieve or at least achieve partially the desired effect. The term "therapeutically effective dose" is an amount that is sufficient to treat the disease. Amounts of the dose will depend upon the type of cancer to be treated, as well as the stages of the cancer (I-IV).

By "administration at certain intervals" means, for example, that the chimeric monoclonal antibody or antibody-like molecule of the present invention may be administered first, followed by administration of the drugs, radioisotopes, toxins or immunogenic killer cells at an interval later; i.e., 30 minutes, 1 hour, 4 hours, 24 hours later. It also accommodates a situation when the drugs, radioisotopes, toxins or immunogenic killer cells are administered first and then the chimeric monoclonal antibody of the present invention is administered at a time interval later; i.e., 30 minutes, 1 hour, 4 hours, 24 hours later.

The present invention is directed to novel monoclonal, chimeric or humanized, antibodies, fragments thereof or antibody-like molecules which bind both human acidic and basic ferritin and their use as therapeutic agents either alone, or with drugs, radioisotopes, toxins, immune killer cells or combinations thereof simultaneously or within certain time periods or conjugated to drugs, radioisotopes, toxins, immune killer cells or combinations thereof. The present invention is further directed toward nucleic acid sequences which encode the monoclonal, chimeric or humanized, antibodies, fragments thereof or antibody-like molecules and their expression in recombinant hosts.

More specifically the present invention is directed toward monoclonal, chimeric or humanized, antibodies, fragments thereof or antibody-like molecules which specifically bind human acidic and basic ferritin and are derived from parts of the murine AMB8LK antibody.

Murine antibody AMB8LK is a murine antibody that was obtained according to the procedure of Kadouche et al "Analysis of various isoferritins with monoclonal antibodies." C R Seances Acad Sci III: 295 (6) 443-448 (1982). Basically after immunization of female Balb/c mice with ferritin extracted from human spleen, spleen cells of the best responders were fused with murine Sp20 myeloma cells using polyethylene glycol 4000 according to standard protocols and selected hybridomas were cloned, expanded and cultured in vitro. AMB8LK was selected for its high affinity of $5.1 \times 10^{-9}$ M, and its specificity for human ferritin.

However, while the murine antibody AMB8LK possesses functional properties which render it suitable as a therapeutic agent, it also is recognized as a foreign antibody in humans and hence is rapidly removed from the circulation. Therefore, higher doses of the murine monoclonal antibody are required for the patient to be treated. This may result in the patient having systemic inflammatory effects.

Therefore, the present invention resolves the problems associated with murine monoclonal antibodies by providing, chimeric or humanized, monoclonal antibodies, fragments thereof or antibody-like molecules having the heavy variable and light variable regions of the murine monoclonal antibody AMB8LK, and particularly with a chimeric monoclonal antibody comprising the heavy variable and light variable regions of the murine monoclonal antibody AMB8LK, a constant heavy region 1 of human Fab' 2-3 cysteine, a human kappa constant light region and human constant heavy chain regions from human IgG1 or IgG4.

In a first aspect, the invention relates to a polypeptide comprising, from N-terminal to C terminal, SEQ ID NO:30, SEQ ID NO:28 and SEQ ID NO:26 (to form a VH domain) or a polypeptide comprising from N-terminal to C terminal, SEQ ID NO:20, SEQ ID NO:22 and SEQ ID NO:24 (to form a VL domain). In a particular embodiment, applying to both, but independently, VH and VL domains, the different SEQ ID are non-contiguous i.e., that each SEQ ID is separated from the other one(s) by additional amino acid residues. These additional amino acid residues can be of murine origin or in the case of humanized antibody design can be derived from human source, especially human immunoglobulin. In this latter case, SEQ ID NOs 30, 28 and 26 and/or SEQ ID Nos: 20, 22 and 24 are grafted on a human scaffold (such as human VH or VL domains) thus replacing their human counterparts. Therefore, the invention is directed to VL and VH domains of murine origin as well as VL and VH domains having CDR from murine origin and framework from human origin (also called humanized or CDR grafted).

In a particular aspect, the VH domain has the following formula:

Nter.AAn-SEQ ID NO: 30-AAm-SEQ ID NO:28-
AAp-SEQ ID NO:26-AAq.Cter (SEQ ID NO: 47), wherein "-" represent a peptide bond, AA represents any amino acid, and n equals to 25 or 26, m is an integer comprised between 15 to 19, preferably 17, p is an integer comprised between 35 and 40 and q is an integer comprised between 10 and 12, preferably 11. AAn, AAm, AAp and AAq correspond respectively to FR1, FR2, FR3 and FR4 regions of a heavy variable domain, and can be of murine or human origin. In a particular embodiment, AAn, AAm, AAp and AAq are respectively, and independently from each other, SEQ ID NO:32, SEQ ID NO:34, SEQ ID NO:36 and SEQ ID NO:38.

| Nucleotide sequence (SEQ ID) | Protein sequence (SEQ ID) |
| --- | --- |
| AAn caggtgcagctgaaggagtcagga cctggcctggtggcaccctcacag agcctgtccatcacatgcactgtc tct (31) | QVQLKESGPGLVAPSQSLSITC TVS (32) |
| AAm gtacactgggttcgccagcctcca ggaaagggtctggagtggctggga acg (33) | VHWVRQPPGKGLEWLGT (34) |
| AAp tataactcagttctcaaatccaga ctgagcatcagcaaggacaactcc aagagccaagttttgttaaaagtg aacagtctacaaactgatgacaca gccatatattactgt (35) | YNSVLKSRLSISKDNSKSQVL LKVNSLQTDDTAIYYC (36) |
| AAq tggggtcaaggaacctcagtcacc gtctcctca (37) | WGQGTSVTVSS (38) |

In a particular embodiment, the VH domain consists essentially of SEQ ID NO:4.

In a particular aspect, the VL domain has the following formula:

Nter.AAr-SEQ ID NO: 20-AAs-SEQ ID NO:22-AAt-
SEQ ID NO:24-AAv.Cter, (SEQ ID NO: 48)

wherein "-" represent a peptide bond, AA represents any amino acid, and r equals to 25 or 26, s is an integer comprised between 15 to 19, preferably 17, t is an integer comprised between 35 and 40 and v is an integer comprised between 10 and 12, preferably 11. AAr, AAs, AAt and AAv correspond respectively to FR1, FR2, FR3 and FR4 regions of a light variable domain, and can be of murine or human origin. In a particular embodiment, AAr, AAs, AAt and AAv are respectively, and independently from each other, SEQ ID NO:40, SEQ ID NO:42, SEQ ID NO:44 and SEQ ID NO:46:

| Nucleotide sequence (SEQ ID) | Protein sequence (SEQ ID) |
| --- | --- |
| AAr caaattgttctcacccagtctcca gcaatcctgtctgcatctctaggg gaggagatcaccctaacctgcagt gccagc (39) | QIVLTQSPAILSASLGEEITLT CSAS (40) |
| AAs atgcactggtaccagcagaagtca ggcacttctcccaaactcttgatt tat (41) | MHWYQQKSGTSPKLLIY (42) |
| AAt aacctggcttctggagtcccttct cgcttcagtggcagtgggtctggg acctttattctctcacaatcagc agtgtggaggctgaagatgctgcc gattattactgc (43) | NLASGVPSRFSGSGSGTFYSLT ISSVEAEDAADYYC (44) |
| AAv ttcggctcggggacaaagttggaa ataaaacgg (45) | FGSGTKLEIKR (46) |

In a particular embodiment, the VL domain consists essentially of SEQ ID NO:2.

In a particular embodiment, a polypeptide comprising a VL domain as defined above, such as SEQ ID NO:2 also comprises a kappa or a lambda chain, such as SEQ ID NO:12, to form a light chain. Thus, the C-terminal part of the VL domain is genetically linked to the N-terminal part of SEQ ID NO: 12, possibly via a linker sequence. In a particular aspect, the VL domain of the invention is linked in its N-terminal part to a signal peptide such as the one having SEQ ID NO:14.

In another aspect, a polypeptide comprising a VH domain of the invention, such as SEQ ID NO:4 also comprises a CH1 constant region, such as SEQ ID NO:6. Thus, the C-terminal part of the VH domain is genetically linked to the N-terminal part of SEQ ID NO: 6, possibly via a linker sequence. In a particular embodiment, a sequence comprising a VH domain (such as SEQ ID No:4) and SEQ ID NO:6 also comprises a human Fc region, such as SEQ ID Nos 8 or 10 or a murine Fc region such as SEQ ID No: 18, to form a heavy chain. In that case, the SEQ ID NO:8, 10 or 18 is genetically linked by its N-terminal part to the C-terminal part of SEQ ID NO:6. Independently or in combination with the above embodiments, the VH domain of the invention is linked in its N-terminal part to a signal peptide such as the one having SEQ ID NO:16.

Particular light and heavy chains of the present invention are:
  a light chain polypeptide comprising from the N-terminal to the C-terminal, a VL domain of the invention, especially SEQ ID NO:2, and SEQ ID NO:12, and
  a heavy chain polypeptide comprising, from the N-terminal to the C-terminal, a VH domain, such as SEQ ID NO:4, SEQ ID NO:6 and a human Fc region, such as a sequence selected from SEQ ID NO:8, SEQ ID NO:10 and SEQ ID NO:18.

Therefore, the present invention relates to a chimeric monoclonal four-chain anti-ferritin antibody comprising two light chains comprising at least a variable light domain (VL) of the invention, of murine origin or having CDR from murine origin and framework from human origin, and particularly the variable light domain as defined in SEQ ID NO: 2 or a variant thereof, and two heavy chains comprising at least a variable heavy domain (VH) of the invention, of murine origin or having CDR from murine origin and framework from human origin, and particularly the variable heavy domain as defined in SEQ ID NO: 4 or variant thereof. The combination of these VH and VL domains forms the ferritin binding site. In a particular embodiment, the variable light domain of the chimeric anti-ferritin monoclonal antibody is the one as defined in SEQ ID NO:2 and/or the variable heavy domain of the chimeric anti-ferritin monoclonal antibody is the one as defined in SEQ ID NO:4.

In a particular aspect of the invention, a chimeric anti-ferritin monoclonal antibody comprises, besides a variable light and heavy domains of the invention (such as SEQ ID Nos 2 and 4 respectively), at least a constant human CH1 region, such as a sequence of SEQ ID NO:6 and/or a lambda or kappa region, such as SEQ ID NO:12. Therefore, SEQ ID NO:6 is genetically linked to the variable heavy domain (such as SEQ ID NO:4) and/or SEQ ID NO:12 is genetically linked to the variable light domain (e.g. SEQ ID NO:2).

Besides the light and heavy domains derived from the variable region of AMB8LK, the chimeric monoclonal antibody of the present invention also includes the constant heavy region 1 of Fab'2-3 cyst of SEQ ID NO: 6, as well as the human kappa light constant region of SEQ ID NO: 12 and a heavy constant Fc region, such as the human gamma 1 constant region (SEQ ID No; 8) or the human gamma 4 constant region (SEQ ID NO: 10) or the murine γ2a constant region (SEQ ID NO: 18).

The invention also relates to a humanized monoclonal antibody in which the light chains are a hybrid of murine CDR and human FR, and/or the heavy chains are a hybrid of murine CDR and human FR. In another aspect, the humanized monoclonal antibody consists of:
  two human light chains in which the CDR1, CDR2 and CDR3 have been respectively replaced by SEQ ID NO:20, SEQ ID NO:22 and SEQ ID NO:24, and/or
  two human heavy chains in which the CDR1, CDR2 and CDR3 have been respectively replaced by SEQ ID NO:30, SEQ ID NO:28 and SEQ ID NO: 26.

Briefly, a human immunoglobulin sequence is isolated from databases for its high sequence similarity with the CDR and/or FR domains of the murine antibody, especially the CDR and/or FR domains as defined by their SEQ ID in the present application. At least one, preferably all, CDR of the VL domain and/or the VH domain of the human immunoglobulin sequence is(are) replaced by the corresponding murine CDR, either by genetic engineering or by chemical synthesis of the full-length sequence. Optionally, tridimensional in silico analysis can be carried out to modify (by substitution, addition and/or deletion) one or more amino acids of the human framework by the corresponding amino acid(s) found at the same position(s) in the murine framework (independently in the VL and VH domain).

Are also encompassed, in the invention, functional fragments of this four-chain, chimeric and humanized, monoclonal antibody, provided that these fragments still bind the ferritin epitope. These fragments include Fv fragment (non-covalent association of the VH and VL domains of the invention) and Fab fragment.

The invention is also directed to molecules based upon Fab fragment as defined above, such as bispecific or trispecific antibodies (see definition above), or bifunctional or trifunctional antibodies. In a particular embodiment, a Fab as defined above is linked to a ligand such a cytokine, a receptor or any protein of interest, to form a bifunctional antibody.

The invention also relates to antibody-like molecules as defined above and comprising at least one variable light domain (VL) of the invention, murine or human/murine hybrid, and particularly the variable light domain as defined in SEQ ID NO: 2 or a variant thereof in combination with at least one variable heavy domain (VH) of the invention, murine or human/murine hybrid, and particularly the variable heavy domain as defined in SEQ ID NO: 4.

In a particular embodiment, the C-terminal part of the variable light domain (VL) of the invention is linked (directly or via a linker) to the N-terminal part of the variable heavy domain (VH) of the invention, to form a scFv. In another embodiment of scFv, the C-terminal part of the variable heavy domain (VH) of the invention is linked (directly or via a linker) to the N-terminal part of the variable light domain (VL) of the invention. These scFv can then be used to form Bis-scFv or diabody, with other scFv recognizing the same or a different epitope and/or antigen. All other molecules based on these scFv can also be envisaged by the person skilled in the art, as long as said antibody-like molecule retains the ferritin binding activity.

In another aspect, the present invention is directed to a chimeric anti-ferritin monoclonal antibody comprising:
  two heavy chains comprising a VH domain sequence encoded by a polynucleotide comprising from 5' to 3' SEQ ID NO:29, SEQ ID NO:27 and SEQ ID NO:25, and
  two light chains comprising a VL domain sequence encoded by a polynucleotide comprising from 5' to 3', SEQ ID NO:19, SEQ ID NO:21 and SEQ ID NO:23.

In another aspect, the VL domain polynucleotide consists essentially of SEQ ID NO:1 and/or the VH domain polynucleotide consists essentially of SEQ ID NO:3.

A particular chimeric anti-ferritin monoclonal antibody, for example, comprises:

two heavy chains encoded by a polynucleotide comprising from 5' to 3' SEQ ID NO:29, SEQ ID NO:27 and SEQ ID NO:25 linked to a polynucleotide encoding for a CH1 constant region such as SEQ ID NO:5 linked to a polynucleotide encoding a human Fc region such as the one selected from the group consisting of SEQ ID NO:7 and SEQ ID NO:9 and two light chains encoded by a polynucleotide comprising from 5' to 3' SEQ ID NO:19, SEQ ID NO:21 and SEQ ID NO:23 linked to a polynucleotide encoding for a lambda or kappa region such as SEQ ID NO:11.

In yet another aspect, the heavy chain is encoded by a polynucleotide comprising, from 5' to 3', SEQ ID NO:3 linked to SEQ ID NO:5 linked to a polynucleotide encoding a human Fc region such as the one selected from the group consisting of SEQ ID NO:7 and SEQ ID NO:9. In another aspect, the light chain is encoded by a polynucleotide comprising from 5' to 3' SEQ ID NO:1 linked to SEQ ID NO:11.

In yet another aspect, the monoclonal, chimeric or humanized, anti-ferritin antibody or fragments thereof as well as the antibody-like molecules of the present invention are coupled to a bioactive agent such as a drugs, radioactive isotopes, toxins, or immune killer cells such as natural killer cells or natural killer T cells. This coupling may be through linkers such as amino acids, β-glucuronide linkers such as those described in Jeffrey et al "Development and Properties of β-Glucuronide linkers for Monoclonal Antibody-Drug conjugates, Bioconjugate Chem. 17 (3) 831-840 (2006) and U.S. Pat. No. 7,098,308.

Drugs that can be either administered with the monoclonal antibody or the antibody-like molecule of the present invention or conjugated to this monoclonal antibody or the antibody-like molecules include alkylating agents such as nitrogen mustards, chlorambucil, chloromethane, cyclophosphamide isofamide, melphalen and the like; nitrosouces such as carmustine, fotemustine, lomustine and the like; platinum drugs such as cisplatinum, oxaliplatin, BBR3464, Busulfan, ThioTepa and the like; antimetabolites such as folic acid drugs of aminopterin, methotrexate and the like; purine drugs such as cladribine, clofarabine and the like; and pyrimidine drugs such as fluorouracil, capecitabine, cytarabine, floxuridine, gemcitabine and the like. Mixtures of these drugs can also be used with the monoclonal antibody or the antibody-like molecule of the present invention, depending on the type of cancer to be treated. For instance, gemcitabine and paclitaxel can be administered to patients having breast cancer with the monoclonal antibody or the antibody-like molecule of the present invention.

Radioactive isotopes that can be conjugated to monoclonal antibodies or antibody-like molecules include gamma, beta, alpha, alpha-beta and beta-gamma emitters as defined in the following Table:

| Radioisotope | Emitted radiation | Note |
|---|---|---|
| $^{211}At$ | Alpha | |
| $^{213}Bi$ | Alpha-Beta-Gamma | Use for alpha radiation |
| $^{51}C$ | Gamma | |
| $^{64}Cu$ | Beta-Gamma | |
| $^{165}Dy$ | Beta | |
| $^{169}Er$ | Beta | |
| $^{18}F$ | Beta-Gamma | |
| $^{68}Ga$ | Beta-Gamma | |
| $^{67}Ga$ | Beta-Gamma | Use for gamma radiation |

-continued

| Radioisotope | Emitted radiation | Note |
|---|---|---|
| $^{166}Ho$ | Beta-Gamma | Use for both types of radiations |
| $^{111}In$ | Gamma | |
| $^{123}I$ | Gamma | |
| $^{125}I$ | Beta-Gamma | Use for both types of radiations |
| $^{131}I$ | Beta-Gamma | Use for both types of radiations |
| $^{192}Ir$ | Beta-Gamma | |
| $^{59}Fe$ | Beta-Gamma | |
| $^{177}Lu$ | Beta-Gamma | |
| $^{32}P$ | Beta | |
| $^{42}K$ | Beta-Gamma | |
| $^{186}Re$ | Beta-Gamma | |
| $^{188}Re$ | Beta-Gamma | Use for beta radiation |
| $^{153}Sm$ | Beta-Gamma | Use for beta radiation |
| $^{75}Se$ | Gamma | |
| $^{24}Na$ | Beta-Gamma | |
| $^{89}Sr$ | Beta | |
| $^{99m}Tc$ | Gamma | |
| $^{201}Ti$ | Beta-Gamma | |
| $^{133}Xe$ | Beta | |
| $^{90}Y$ | Beta | |

These isotopes can be linked to the monoclonal, chimeric or humanized, anti-ferritin antibody or fragments thereof as well as the antibody-like molecules of the invention through chelating agents such as bifunctional ligands, diethylenetriaminepentaacetic acid (DTPA) and any of its derivatives, 1,4,7,10-tetraazacyclododecane-1,4,7,10-tetraacetic acid (DOTA) and any of its derivatives, or any macrocyclic ligand, 1,3 bis[N—[N-(2-aminoethyl)-2-aminoethyl]-2-aminoacetamido]-propane-N,N,N',N'',N''',N'''',N''''',N''''''-octaacetic acid (LiLo), N—(S-acetylmercaptoacetyl)(p-NCS) phenylalanylglycylglycine ethyl ester (for $^{99m}TC$ or $^{186}Re$ labeling), 5,7-dioxo-1,11-carboxymethyl)-1,4,8,11-tetraazacyclotridecane, 1,4,7,10-tetraazacyclotridecane-N,N',N'',N'''-tetra-acetic acid (TRITA) 1,4,8,11-tetraaxacyclotetra-decane-N,N', N'',N'''-tetraacetic acid (TETA), 1,5,9,13-tetraazacyclohexadecane-N,N',N'''',N''''''-tetraacetic acid (HETA).

Examples of toxins include Coley toxins, ricin A chain, PAP (pokeweed antiviral toxin), Staphylococcus aureus bacteria (SEB), Pseudomonas exotoxin, and the like. The toxins can be coupled to the monoclonal antibody of the present invention or they can be given simultaneously therewith.

Besides drugs and radioisotopes, other biological molecules can also be coupled to the monoclonal, chimeric or humanized, anti-ferritin antibody or fragments thereof as well as the antibody-like molecules of the present invention such as enzymes, nucleic acids, anti-sense RNAs, siRNA, biotin, streptavidin or avidin molecules to improve antibody binding specificity, or biological molecules that can bind to a specific cell type and the like.

It is noteworthy that at least two monoclonal, chimeric or humanized, antibodies, fragments or antibody-like molecules of the invention can be combined in any combination in a single composition.

In another aspect the present invention relates to a composition comprising (a) a chimeric anti-ferritin monoclonal antibody, a humanized monoclonal antibody, a functional fragment, a bispecific monoclonal antibody, a trispecific monoclonal antibody, a bifunctional antibody, a scFv molecule, a Bis-scFv or a diabody of the invention, such as a monoclonal antibody comprising as a light chain SEQ ID Nos. 2 and 12, and as a heavy chain SEQ ID Nos 4, 6 and 8 or SEQ ID Nos. 4, 6 and 10, and (b) a pharmaceutically acceptable vehicle.

Pharmaceutically acceptable vehicles include carriers, excipients and stabilizers. The formulations can be prepared as set forth in Remington's Pharmaceutical Sciences 16th edition, Osol A. editor (1980). Examples of carriers, excipients and stabilizers include saline, PBS, buffers such as phosphate, citrate and other organic acids; antioxidants such as ascorbic acid, low molecular weight polypeptides; proteins such as serum albumin, immunoglobulins, gelatins; hydrophilic polymers such as PVP; amino acids of glycine, glutamine, arginine, lysine or asparagines; carbohydrates such as glucose, mannose or dextrins; sugar alcohols including mannitol or sorbitol; salt-forming counterions such as sodium and/or nonionic surfactants such as Tween®.

The pharmaceutical composition can be administered by infusion, intravenously, intraperitonally, intramuscularly intraarterially or by sustained release systems such as liposomes or polylactic-coglycolic acid. Sustained release systems are described in U.S. Pat. No. 5,255,212 and Lewis, "Controlled release of bioactive agents from lactide/glycolide polymer." In M. Chasin and R. Langer (Eds.) Biodegradable Polymers as Drug Delivery Systems (Marcel Decker: New York, 1990).

Dosages and drug concentrations can be determined depending on the particular use envisioned, the stage and type of cancer to be treated, as well as the body weight of the mammal. Standard pharmaceutical procedures can be used to determine the toxicity and therapeutic efficacy by using cell cultures or experimental animals. Usually the $LD_{50}$ (lethal dose to 50% of the population) and the $ED_{50}$ (the therapeutically effective dose in 50% of the population) can be determined. The therapeutic index is the dose between the toxic and therapeutic effects.

The data obtained from the above assays can be used in a range of dosage for human and mammalian use. Generally from 1 ng/kg to 100 mg/kg doses are administered.

In another embodiment, the present invention relates to a method of delivering a drug, radioactive materials, toxins, immune killer cells or combinations thereof to cells containing basic and acidic ferritin, said method comprising administering to a mammal in need of such treatment a composition comprising (a) a chimeric anti-ferritin monoclonal antibody, a humanized monoclonal antibody, a functional fragment, a bispecific monoclonal antibody, a trispecific monoclonal antibody, a bifunctional antibody, a scFv molecule, a Bis-scFv or a diabody of the invention, in particular an antibody comprising as a light chain SEQ ID Nos. 2 and 12, and as a heavy chain SEQ ID Nos 4, 6 and 8 or SEQ ID Nos. 4, 6 and 10 and (b) a composition selected from the group of drugs, radioactive isotopes, toxins, immune killer cells and combinations thereof, wherein said composition is in a pharmaceutically acceptable carrier.

The chimeric construct having SEQ ID NO: 8 has ADCC effector function, to enhance the performance of this monoclonal antibody, a radioactive isotope or an antimetabolite drug such as gemcitabine can also be used in the formulation.

As discussed above the drug, radioactive isotopes, toxins immune killer cells or combinations thereof may be attached to the monoclonal antibody, the fragment or the antibody-like molecule of the invention, either through a chelating agent or a linker or they can be administered simultaneously or at specific intervals with the monoclonal antibody, the fragment or the antibody-like molecule of the invention.

In yet another aspect, the present invention relates to a method of treating a cancer selected from the group of pancreatic cancer, Hodgkin's lymphoma, Kaposi's sarcoma and hepatocellular carcinoma said method comprising administering to a mammal in need of such treatment (a) a chimeric anti-ferritin monoclonal antibody, a humanized monoclonal antibody, a functional fragment, a bispecific monoclonal antibody, a trispecific monoclonal antibody, a bifunctional antibody, a scFv molecule, a Bis-scFv or a diabody of the invention, in particular an antibody comprising as a light chain SEQ ID Nos. 2 and 12, and as a heavy chain SEQ ID Nos 4, 6 and 8 or SEQ ID Nos. 4, 6 and 10, and (b) a pharmaceutically acceptable carrier and optionally a composition selected from the group of drugs, radioactive isotopes, toxins, immune killer cells and combinations thereof.

In another aspect, the present invention relates to nucleic acids (or polynucleotides) encoding any variable light domain (VL), any variable heavy domain (VH), any light chain, any heavy chain or any polypeptide as described in the present application.

In another aspect, a nucleic acid encoding a variable light domain comprises, from 5' to 3', SEQ ID NO: 19, SEQ ID NO:21 and SEQ ID NO:23. In yet another aspect, these SEQ ID are non contiguous. In another embodiment, the nucleic acid consists essentially of or comprises SEQ ID NO:1 or any polynucleotide variant thereof.

In another embodiment, a nucleic acid encoding a variable heavy domain comprises, from 5' to 3', SEQ ID NO: 29, SEQ ID NO:27 and SEQ ID NO:25. In yet another embodiment, these SEQ ID are non contiguous. In another aspect the nucleic acid consists essentially of or comprises SEQ ID NO:3 or any polynucleotide variant thereof.

In another embodiment, a polynucleotide encoding a variable light domain of the invention (such as SEQ ID NO:1) also comprises a kappa or lambda chain sequence, such as SEQ ID NO:11. Thus, the 3' part of the variable light domain polynucleotide is genetically linked to the 5' part of SEQ ID NO: 11, possibly via a linker sequence. In another aspect, the variable light domain polynucleotide is linked in its 5' part to a signal peptide such as the one having SEQ ID NO:13.

In yet another embodiment of the present invention, a polynucleotide encoding a variable heavy domain of the invention (such as SEQ ID NO:3) also comprises a human CH1 constant region sequence, such as SEQ ID NO:5; Thus, the 3' part of a variable heavy domain polynucleotide is genetically linked to the 5' part of SEQ ID NO: 5, possibly via a linker sequence. In yet another embodiment, a polynucleotide comprising a polynucleotide encoding a variable heavy domain of the invention (such as SEQ ID NO:3) and SEQ ID NO:5 also comprises a sequence encoding a human Fc region, such as SEQ ID Nos 7, 9 or a murine Fc region (SEQ ID No:17). In that case, the SEQ ID NO: 7, 9 or 17 is genetically linked by its 5' part to the 3' part of SEQ ID NO:5. Independently or in combination with the above embodiments, a variable heavy domain polynucleotide is linked in its 5' part to a signal peptide such as the one having SEQ ID NO: 15.

Particular nucleic acids are:
a polynucleotide comprising from 5' to 3' a variable light domain polynucleotide of the invention (such as SEQ ID NO:1) and SEQ ID NO:11,
a sequence comprising from 5' to 3' SEQ ID NO:13, a variable heavy domain polynucleotide of the invention and SEQ ID NO:11,
a sequence comprising from 5' to 3' a variable heavy domain polynucleotide of the invention (such as SEQ ID NO:3), SEQ ID NO:5 and a polynucleotide encoding a Fc region, such as a sequence selected among SEQ ID NO:7, SEQ ID NO:9 and SEQ ID NO:17, and
a sequence comprising from 5' to 3' SEQ ID NO:15, a variable heavy domain polynucleotide of the invention, SEQ ID NO:5 and a polynucleotide encoding a Fc region, such as a sequence selected among SEQ ID NO:7, SEQ ID NO:9 and SEQ ID NO:17.

Another sequence is the one encoding the ScFv disclosed above and having a variable light domain polynucleotide of the invention (such as SEQ ID NO:1) genetically linked to a variable heavy domain polynucleotide of the invention (such as SEQ ID NO:3), provided the scFv retains the ferritin-binding activity.

Isolated nucleic acids having at least 95% or 98% or 99% sequence identity to variable heavy and light domain polynucleotides of the invention, and to SEQ ID NOS. 1 and 3, are also encompassed in an aspect of the present invention. In the nucleic acids or polynucleotides defined above, the various SEQ ID may be replaced, individually and independently one from the other, by a variant having at least 85%, 90%, 95% or 99% sequence identity with SEQ ID NO: 1, 3, 5, 7, 9, 11, 13, 15, 17, 19, 21, 23, 25, 27, 29, 31, 33, 35, 37, 39, 41, 43 and 45, with the proviso that said various domains encoded by these nucleotide sequences enables the resulting monoclonal antibody or antibody-like molecules to keep the AMB8LK binding activity to human acidic and basic ferritin. Polynucleotide variants are variants containing conservative substitutions i.e., a nucleotide substitution that do not modify the nature of the encoded amino acid. Other particular nucleotide substitution are semi-conservative i.e., that the encoded amino acid is from the same class as the original amino acid, as detailed above.

The invention further relates to nucleic acids encoding the polypeptide or which hybridize, optionally over the full-length sequence, to a DNA sequence consisting of the nucleotide sequence encoding such polypeptide under stringent conditions. These stringent conditions are described by Sambrook et al, Molecular Cloning Manual, $3^{rd}$ edition (2001), i.e., as an example, the following conditions: hybridization buffers: 2×SSC, 10×Denhardts solution (Ficoll 400 & PEG & BSA, ratio 1:1:1), 0.1% SDS, 5 mM EDTA, 50 mM $Na_2HPO_4$, 250 μg/ml herring sperm DNA, 50 μg/ml of t-RNA or 0.25 M of sodium phosphate buffer with a pH of 7.2, 1 mM EDTA, 7% SDS;

Hybridization temperature: 60° C.;
Washing buffer: 2×SSC, 0.1% SDS;
Washing temperature: 60° C.

The invention further relates to recombinant nucleic acid vectors comprising at least one nucleic acid sequence as defined in the present application, and in vectors comprising a variable heavy domain polynucleotide of the invention and/or a variable light domain polynucleotide of the invention, and vectors comprising SEQ ID NO:1 and/or SEQ ID NO:3.

For example a vector comprising a nucleic acid encoding a light and a heavy chains of the invention which comprises the heavy variable and light variable domains of the murine monoclonal antibody AMB8LK, a constant heavy region 1 of human Fab' 2-3 cysteine, a human kappa constant light region and an Fc region constant heavy chain region from human IgG1 or IgG4 or a murine γ2a.

The vectors can be cloning vectors such as plasmids or modified viruses, but can also be bacteriophages such as lambda derivatives, pBP322, pUC plasmid derivatives of the Bluescript vector. In another embodiment, the nucleic acids are inserted into baculovirus plasmid vectors such as pVL941.

In yet another embodiment, the vector comprises a nucleic acid encoding the light chain of the invention. In another aspect, the vector comprises a nucleic acid encoding the heavy chain of the invention. In another embodiment, the vector comprises a nucleic acid encoding the heavy chain and the light chain of the invention.

Methods of producing antibodies or antibody-like molecules of the present invention comprising growing cells containing the above recombinant vectors is also an aspect of the present invention. In this regard, the cells can be CHO cells, *E. coli*; yeast cells, VERO cells, HELA cells, COS cells, CR cells: 1650, W138, BHK, HepG2, 3T3, A549, PC12, K562, 293 cells, insect cells such as *Spodotera frugiperda Sf9* cells (ATCC 358 CRL 1711), Cv1 cells and the like. According to the nucleic acid inserted in the vectors, and the number of vectors transduced into the cells, the protein or the antibody or the antibody-like molecule is expressed in the cell and can then be recovered by methods known in the art such as via columns.

Any expression regulatory sequences, such as promoters can be used in the vectors of the present invention. Examples of such promoters include SV40 early promoters, the promoter contained in the 3'long terminal repeat of Rous sarcoma virus, the herpes thymidine promoter, the regulatory sequence of the mettallothionein gene, prokaryotic expression vectors such as the beta-lactamase promoter or the lac promoter and the like, as well as polyhedrin promoter (Ph) or promoter 10 (both adapted for baculovirus expression).

The chimeric monoclonal antibodies, fragments or antibody-like molecules of the present invention can be synthesized using chemical methods based on the sequences described herein. These methods are known in the art and are described, for example in Hunkapiller et al., Nature 310:105-111.

The chimeric monoclonal antibodies, fragments or antibody-like molecules of the present invention can be obtained by recombinant techniques. Therefore, the invention also relates to monoclonal antibodies, fragments or antibody-like molecules as defined above, obtained by expression of at least one nucleic acid of the invention. In this case, construction of suitable vectors containing the desired coding and control sequences employ standard ligation techniques. Isolated plasmids or DNA fragments are cleaved tailored and relegated in the form desired to form the plasmid required.

Cleavage of the sequences is completed using appropriate endonucleases (restriction enzymes) in a suitable buffer. These cleavage techniques are well known to those skilled in the art. If blunt ends are required the preparation is treated at 15° C. for 15 minutes with 10 units of *E. coli* DNA Polymerase (Klenow fragment), phenol-chloroform extracted and ethanol precipitated.

Size separation of the fragments can be carried out as described by Goeddel, D. et al Nucleic Acid Res. 8:4057 (1980). For ligation approximately equimolar amounts of the desired components suitably end tailored to provide correct matching are treated with 10 units T4 DNA ligase per 0.5 μg DNA.

The expression vectors constructed are then used to transform suitable cells. The light and heavy chains are transformed in a same cell, either two vectors each bearing the light or the heavy chain or a single vector containing both genes and able to express both the light and heavy chains.

The cells are then grown under conditions for production of the desired protein. The protein is then recovered from the cell culture by methods known in the art. The recovery process depends on the type of cells used for protein production. When light and heavy chains are coexpressed the isolation procedure is planned to recover the constituted antibody. When signal peptides are present in the N-terminal part of the heavy and light variable domains, they are cleaved into the cells, before assembly of the light and heavy variable domains and if appropriate chains comprising them.

For constructing the monoclonal antibodies, fragments or antibody-like molecules, the desired portions of the genes encoding the light and heavy chains (or variable light and heavy domains) from suitable sources are religated using ligases. Thus, the sources of the heavy chain gene and the light chain gene (or VH and VL) which encode the variable portions produced by the murine hybridoma AMB8LK are recovered and cloned. From this culture and gene fragments encoding the constant regions of the heavy and light chains of human gamma 1, human gamma 4, human kappa and Fab'2 are recovered and cloned from human myeloma cells. Suitable restriction enzymes are used to ligate the variable portions to the light portions of the mouse gene to the constant portions of the human gene for each of the two chains.

Once the monoclonal antibodies, fragments or antibody-like molecules of the invention are fabricated as described above with or without drugs, radioisotopes, toxins, natural killer cells and combinations thereof, they can be tested for immunoreactivity with human ferritin using ELISA or RIA assays as set forth in the Examples. This is especially helpful when variants of the sequences are used and/or fragments.

A number of embodiments of the invention have been described. Nevertheless, it will be understood that various modifications may be made without departing from the spirit and scope of the invention.

EXAMPLE 1

Monoclonal Anti-Ferritin Antibody AMB8LK

AMB8LK is a monocolonal IgG1 anti-ferritin antibody at 1-10 mg/ml in PBS. This antibody was obtained as previously described by Kadouche et al "Analysis of various isoferritins with monoclonal antibodies]. C R Seances Acad Sci III 1982; 295 (6):443-8, after immunization of female Balb/c mice with ferritin extracted from human spleen. Spleen cells of the best responders were fused with murine Sp2/0 (ATCC Number: CRL-1581) myeloma cells using polyethylene glycol 4000 according to standard protocols and selected hybridomas were cloned, expanded and cultured in vitro. AMB8LK was selected for its very high affinity of $5.1 \times 10^{-9}$ M, and its specificity for human ferritin.

EXAMPLE 2

Conjugation of the DPTA and DOTA Chelates on AMB8LK

The bifunctional chelators pSCN-Bz-DTPA (2-(4-isothiocyanatobenzyl)-diethylenetriaminepentaacetic acid), pSCN-Bz-CHX-A"-DTPA ((R)-2-amino-3-(4-isothiocyanantophenyl)propyl]-trans-(S,S)-cyclohexane-1,2-diamine-pentaacetic acid) and pSCN-Bz-DOTA (2-(4-isothiocyanatobenzyl)-1,4,7,10-tetraazacyclododecane-1,4,7,10-tetraacetic acid) (FIG. 10) were purchased from Macrocyclics. These ligands were then conjugated to AMB8LK as previously described by Cooper et al., "Conjugation of chelating agents to proteins and radiolabeling with trivalent metallic isotopes." Nature Protocols 2006; 1:314-17. Briefly, the antibody was preincubated at room temperature with EDTA, transferred to HEPES 0.1 M, pH8.5 and the concentration was adjusted to 5-10 mg/ml. Solutions of the chelators in ethanol were added drop wise to the antibody solution at 50 equivalents of chelate/antibody, unless stated otherwise. The reaction was allowed to proceed overnight at 37° C. The buffer was then changed into ammonium acetate buffer 0.1M, pH 6 and removal of the unbound chelator was performed using ultrafiltration with a molecular weight cutoff of 30 kDa. The final concentration of the antibody was determined by UV absorbance at 280 nm. For ease of description Bz-DTPA-AMB8LK is described below as DTPA-AMB8LK; the Bz-CHX-A-DTPA-AMB8LK as CHX-DPTA"-AMB8LK and the Bz-DOTA-AMB8LK is designated DOTA-AMB8LK.

The number of chelates conjugated to the antibody was determined using a $^{57}Co$ assay as described (Meares et al., "Conjugation of antibodies with bifunctional chelating agents: isothiocyanate and bromoacetamide reagents, methods of analysis, and subsequent addition of metal ions." Anal Biochem 1984; 142 (1):68-78). A constant amount of $^{57}CoCl_2$ of known specific activity (ICN, Basingstoke, Hamps, London) was incubated with increasing amounts of conjugated-antibody for 1-2 hours at room temperature or 37° C. for the DOTA-conjugate. The reaction was stopped by adding 50 mM EDTA in 0.1 ammonium acetate, 2-10% vol/vol. The solutions were analyzed by instant thin-layer chromatography (ITLC) (Pall Life Sciences, Portsmouth, U.K.) using the EDTA solution as the mobile phase. Unbound Co migrated to the solvent front, whereas $^{57}Co$-labeled antibody remained at the origin of the strip. The activity in each portion of the strip was measured with a 1282 gamma counter (LKB, Wallac). Linear regression of the results using the equation % of bound activity=f(Ab amount) allowed the determination of the mean number of chelates conjugated to each molecule of antibody.

Optimal conditions for chelator conjugation were determined after incubating equal amounts of AMB8LK with increasing amounts of pSCN-Bz-DTPA at 4° C., RT or 37° C. for various times. To achieve a conjugation of circa 3 chelates substitutions per antibody, a chelate per antibody reaction ratio of 50:1 was used, incubated overnight at 37° C. Overnight incubation at room temperature produced a yield of about 1.7 DTPA/antibody (Ab) and incubation at 37° C. for 6 hours, about 1.5 DTPA/Ab. The efficiency of conjugation was similar for the three chelators: effective conjugation of 3 Bz-DTPA per Ab, 3 Bz-CHX-A'-DTPA per Ab and 3.2 Bz-DOTA per Ab were achieved. Less than 4% antibody aggregates were formed during the conjugation process as determined by SE-HPLC.

EXAMPLE 3

Size-Exclusion Chromatography

Size-exclusion high liquid performance chromatography (SE-HPLC) analysis was performed using a Beckman 114M solvent module-pump with a Beckmamn 340 injection module and a Beckman 160 absorbance detector connected to a Raytest gamma radioactivity detector. Stationary phase was a BioSep SEC-53000 column 300×7.8 mm (Phenomex, Cheshire, UK). Isocratic elution with 0.1 M phosphate buffer (0.06 M $Na_2HPO_4$, 0.04 M $NaH_2PO_4$, 2 mM EDTA, pH 7) was used at a flow rate of 0.5 ml/min. Chromatograms were analyzed using Galaxie (Novell) software.

EXAMPLE 4

Radiolabelling with Indium and Yttrium

Indium [($^{111}In$] chloride (gamma emitter), 111 MBq in 500 µl 0.05 HCl was purchased from Mallinckrodt (Petten, Netherlands). Yttrium [$^{90}y$] chloride (pure beta emitter) 185 MBq, was acquired from MDS Nordion (Fleurs, Belgium) and dissolved in HCL 0.05 M to give a final volume of 100 µl.

The pH of indium or yttrium was adjusted to 6 by adding 0.1 M ammonium acetate, pH 6 (20% of the final volume). The conjugated antibodies were added to obtain a specific activity of 130 MBq/mg antibody (unless stated otherwise) and incubated for 30-60 minutes at room temperature for the DTPA-conjugates or at 37° C. for the DOTA. The labeling reactions typically were performed using 50 µg of antibody with 6.5 MBq of radionuclide. The reaction was then quenched by adding 2-10% vol/vol EDTA 50 mM and PBS was added to produce a concentration of about 10 MBq/ml. Labelling efficiency was determined by TLC using 50 mM EDTA in 0.1 M ammonium acetate, pH 6 as the mobile phase. Under these conditions radiolabelled antibodies have an $R_f=0$ while unbound radionuclide has an $R_f=1$. The percentage activity was measured after cutting the strip in two and counting the activity in each portion in a 1282 gamma counter (LKB, Wallac, Finland). Labelling efficiency was expressed as (cpm origin)/cpm origin+cpm front)×100. Labelling efficiency was also determined by HPLC using an isocratic mobile phase with phosphate buffer, then integrating the peaks with the Galaxie software (Novell).

Increasing the incubation time to 1 hour did not improve significantly the labelling efficiency while increasing the temperature to 37° C. for the DTPA-conjugates improved the labelling efficiency by only 1% compared to labelling at room temperature. After having assessed the time and temperature parameters, specific activities ranging from 40-330 MBq/mg of Ab were tested. No significant difference in the labelling results was observed. The effect of radioactive concentration during the labelling reaction was also studied. The is results of indium labelling using radioactivity concentrations ranging from 100 to 330 MBq/ml demonstrated that within this concentration range, labelling efficiencies were similar.

EXAMPLE 5

In vitro Stability of the Radiolabelled Immunoconjugates

Stability of the $^{111}$In and $^{90}$y-labelled immunoconjugates was assessed in PBS and in plasma, at 4° C. and 37° C., respectively. Radiolabelling was performed as described above, then 4-6 MBq of the radiolabelled-monoclonal antibody was added to PBS or plasma to produce a final volume of 0.4-0.5 ml. 10 µl (0.05 MBq) of the radiolabelled antibody was analyzed by SE-HPLC and 0.5 ml eluate fractions were collected for 30 minutes. The activity in each fraction was counted using a gamma counter and the elution profile was plotted from these results. The percentage of radiolabelled antibody remaining over time was then determined. For the stability study in PBS, in addition to SE-HPLC, ITLC was performed using 50 mM EDTA as the mobile phase.

The two $^{111}$In-DTPA-immunoconjugates stored at 4° C. in PBS showed greater than 98% stability over 7 days, while the $^{111}$In-DOTA conjugate showed 94%. The stability of the $^{90}$y-labelled-antibodies stored in the same conditions was around 80%. In plasma at 37° C., the indium- and yttrium-compounds were stable for at least 7 days (loss of less than 3% of activity).

EXAMPLE 6

Immunoreactivity of these Immunoconjugates on Pure Ferritin: ELISA and RIA

The immunoreactivity of the three immunoconjugates was assessed using an ELISA. Preliminary assays using ferritin (human liver ferritin, Calbiochem) adsorbed overnight at 0.1, 1.5 and 10 µg/ml showed that the optimal ferritin concentration for the assay was 5 µg/ml ferritin. Thus, 5 µg/ml ferritin in PBS was adsorbed on a 96-well plate (Maxisorp, Nunc). The wells were washed with PBS-0.4% Tween-20 then blocked for 2 hours at room temperature with PBS-0.5% BSA, Conjugated antibodies and the unconjugated antibody used as a control were incubated for 2 hours at room temperature in PBS-0.5% BSA, at concentrations ranging from $10^{-8}$ to $10^{-1}$ mg/ml (50 µl per well). Wells were then washed with PBS-0.4% Tween-20 and the secondary antibody (alkaline phosphatase conjugated IgG anti-mouse, Sigma) was added at 1:25,000 dilution in PBS for 1 hour at room temperature. After washings the substrate p-nitrophenyl phosphate tablets, pNPP, Sigma) was added (1 mg/ml pNPP in 0.2 M Tris buffer, 5 mM magnesium chloride). The reaction was quenched after 30 minutes with 3 M NaOH, 1/1 vol/vol. Absorbance was read at 405 nm on a DTX 880 plate reader (Beckman Coulter) and results were analyzed using the GraphPad Prism software (San Diego, Calif.). Results showed a slight decrease in the binding of ferritin of the conjugates compared to that of native antibody (FIG. 11). However, no difference could be noticed between the three compounds.

A solid-phase radioimmunoassay was performed using $^{111}$In- and $^{90}$y-labelled antibodies. Maxisorp tunes (Nunc) were incubated overnight at 4° C. with 1.5 to 10 µg/ml ferritin in PBS. After washing, they were blocked by PBS-0.5% BSA for 2 hours at room temperature. $6.25 \times 10^3$, $12.5 \times 10^3$ and $25 \times 10^3$ CPM (200 µl) of the antibodies were added in the coated tubes. The activity in each tube was counted in the gamma counter, then the tubes were washed three times with PBS-0.4% Tween-20 and the remaining activity counted. The difference between activities with and without the radiolabelled-antibody solutions indicated the percentage of bound-antibody. For evaluation of non specific binding to ferritin, a 100-fold excess of unconjugated antibody was added to the most concentrated radiolabelled-antibody solution. Non specific binding of the antibody was assessed on uncoated tubes. Results showed that regardless of the radionuclide (indium or yttrium), the DTPA-AMB8LK compound had the highest reactivity with ferritin of the three immunoconjugates whereas the DOTA-conjugate had the lowest (Table 1 below). These binding percentages were calculated taking into account small differences in the labelling efficiencies of the three compounds on the day of the experiment.

EXAMPLE 7

Immunoreactivity of the Radiolabelled-Immunoconjugates on CAPAN-1 Cells

Immunoreactivity of the immunoconjugates was assessed on cells expressing ferritin using the method described by Lindmo et al Determination of the immunoreactive fraction of radiolabeled monoclonal antibodies by linear extrapolation to binding at infinite antigen excess. *J Immunol Methods* 1984; 72 (1):77-89.

The CAPAN-1 cells are a relevant model for human pancreatic cancer (Kyriazis et al Human pancreatic adenocarcinoma line Capan-1 in tissue culture and the nude mouse: morphologic, biologic, and biochemical characteristics. *Am J Pathol* 1982; 106(2):250-60.). This cell line was established from a liver metastasis of a human pancreatic ductal adenocarcinoma, is tumorigenic and metastatic in nude mice and over-expresses ferritin. The F(ab)$_2$ fragment of AMB8LK has been shown to bind to CAPAN-1 (Goldstein et al., The design and evaluation of a novel targeted drug delivery system using cationic emulsion-antibody conjugates. *J Control Release* 2005; 108 (2-3):418-32). CAPAN-1 cells were grown in RPMI, 10% foetal calf serum and 2 mM L-glutamine. Cells were harvested at 70-85% confluence using trypsin, washed and resuspended in PBS-0.5% BSA. They were then fixed and permeabilized using the Intrastain kit (rako) following the manufacturer's instructions. Cells were diluted in PBS-0.5% BSA at concentrations ranging from $1.25 \times 10^5$ to $12 \times 10^6$ cells/ml and 500 µl of these suspensions were incubated with a fixed amount of $^{111}$In-labeled-Ab (250 µl, 50 ng/ml, approximately 100,000CPM) for 2 hours at room temperature under agitation. Suspensions were centrifuged at 5,000×rpm for 5 minutes, the cells were washed with PBS-BSA and the activity in the pellets was counted. Nonspecific binding was determined by co-incubation of the radiolabelled-antibody with a 1.000-fold excess of cold antibody. The total radioactive counts added to each tube were divided by the cell-bound counts after subtraction of the non-specifically bound counts. These values were plotted against the reciprocal of cell dilution. After linear regression analysis, the immunoreactive fraction was obtained from the reciprocal of the intercept on the y-axis.

Assays, using non-fixed non-permeabilized CAPAN-1 cells, failed to show binding of the conjugates. However, if the cells were fixed and permeabilized before incubation with the antibody, high levels of specific binding were achieved. The experiments demonstrated that, like pure ferritin, the reactivity of the DTPA conjugate was greater than that of the CHX-DTPA while the DOTA-AMB8LK had the least reactivity on the CAPAN-1 cells (Table 1 below).

TABLE 1

Immunoreactivity of conjugated AMB8LK on ferritin

|  | Pure ferritin[a] | | Cells[b] |
| --- | --- | --- | --- |
|  | $^{111}$In | $^{90}$y | $^{111}$In |
| Bz-DTPA-AMB8LK | 87.0% | 100% | 52% |
| Bz-CHX-A''-DTPA AMB8LK | 74.8% | 98.9% | 43% |
| Bz-DOTA-AMB8LK | 76.8% | 73.2% | 24% |

[a] Ferritin was immobilised at 5 µg/ml on tubes, then the indium or yttrium conjugated antibodies were incubated at three dilutions (3.75 to 15 × 10⁶ CPM) Results are expressed as the mean of the percentage of bound antibody after washing the tubes. Non specific binding of the antibodies were less than 2%.

[b] Five serial dilutions of fixed and permeabilized CAPAN-1 cells were incubated with the three radiolabelled compounds. After washing, the activity bound to the cells was counted in a gamma counter. Results were analysed using the GraphPad software; linear regression analysis of (Total CPM/Bound CPM) = f(cells dilution) were very accurate with $r^2 > 0.99$ for all three conjugates.

As can be seen in Table 2, the liver showed the highest uptake of all the organs, with an uptake of the CHX-DTPA- and the DOTA-AMB8LK of 13-15% of the injected dose (ID), while that of the DTPA-AMB8LK was 7-8%. Other organs showing significant levels of uptake were the bones, especially by the CHX-DTPA-conjugate (4.5±1.5% of the ID after 24 hours; 6.4±2.0% after 72 hours) and the intestine (<4% of the ID for the three conjugates) (Table 2). Uptake in the muscle, lung and kidneys was less than 2%; that in the stomach and spleen less than 1%. Circulating activity in the blood was the lowest for DOTA-AMB8LK (5.7±3.9% of the ID/g after 24 hours and 3.1±2.1% after 72 hours); the activities of the two DTPA conjugates in the blood were similar after 24 h but the subsequent clearance of the CHX-DTPA-AMB8LK was faster than that of the DTPA-AMB8LK (Table 2 below). Based on these results, the DTPA-AMB8LK seemed to be the most promising of the three immunoconjugates despite its relatively slow blood clearance (still 12.6±0.8% of the ID/g 72 hours after injection).

TABLE 2

Biodistribution of $^{111}$In-labelled Bz-DTPA-, Bz-CHX-A'-DTPA and Bz-DOTA-AMB8LK in normal mice

|  | Bz-DTPA-AMB8LK Mean ± SD, n = 4 | | | Bz-CHX-A''-DTPA-AMB8LK Mean ± SD, n = 4 | | | Bz-DOTA-AMB8LK Mean ± SD, n = 4 | | |
| --- | --- | --- | --- | --- | --- | --- | --- | --- | --- |
|  | 24 h | 48 h | 72 h | 24 h | 48 h | 72 h | 24 h | 48 h | 72 h |
| Blood | 15.8 ± 1.2 | 13.3 ± 1.8 | 12.6 ± 0.8 | 16.7 ± 1.6 | 12.3 ± 1.2 | 9.7 ± 1.9 | 5.7 ± 3.9 | 5.6 ± 1.1 | 3.1 ± 2.1 |
| Bone | 2.1 ± 0.4 | 2.6 ± 0.2 | 1.7 ± 1.4 | 4.5 ± 1.5 | 4.4 ± 2.6 | 6.4 ± 2.0 | 1.6 ± 1.3 | 2.3 ± 0.3 | 1.8 ± 0.7 |
| Muscle | 1.4 ± 0.2 | 1.3 ± 0.2 | 1.0 ± 0.4 | 1.4 ± 0.1 | 1.2 ± 0.2 | 1.1 ± 0.1 | 0.6 ± 0.4 | 0.6 ± 0.1 | 0.5 ± 0.2 |
| Liver | 7.0 ± 0.5 | 7.1 ± 1.0 | 7.5 ± 0.5 | 13.5 ± 1.0 | 13.9 ± 2.1 | 12.9 ± 1.9 | 13.6 ± 7.8 | 15.1 ± 2.5 | 14.4 ± 1.1 |
| Lung | 1.2 ± 0.2 | 1.3 ± 0.3 | 1.2 ± 0.3 | 1.7 ± 1.0 | 1.2 ± 0.3 | 1.0 ± 0.5 | 0.7 ± 0.5 | 0.6 ± 0.1 | 0.4 ± 0.3 |
| Stomach | 0.4 ± 0.1 | 0.3 ± 0.1 | 0.3 ± 0.1 | 0.3 ± 0.0 | 0.3 ± 0.0 | 0.2 ± 0.1 | 0.1 ± 0.1 | 0.2 ± 0.1 | 0.1 ± 0.1 |
| Spleen | 0.5 ± 0.0 | 0.5 ± 0.1 | 0.5 ± 0.1 | 0.7 ± 0.0 | 0.7 ± 0.1 | 0.7 ± 0.1 | 0.4 ± 0.2 | 0.5 ± 0.1 | 0.5 ± 0.2 |
| Intestine | 3.2 ± 0.2 | 3.7 ± 0.8 | 2.9 ± 0.3 | 3.9 ± 0.1 | 3.5 ± 0.3 | 2.9 ± 0.3 | 1.7 ± 0.6 | 2.3 ± 0.2 | 1.6 ± 0.5 |
| Kidneys | 1.5 ± 0.1 | 1.3 ± 0.1 | 1.1 ± 0.1 | 1.8 ± 0.1 | 1.4 ± 0.2 | 1.1 ± 0.1 | 0.7 ± 0.4 | 0.7 ± 0.1 | 0.4 ± 0.1 |

EXAMPLE 8

Biodistribution of the Indium- and Yttrium-Radiolabelled Conjugated Antibodies in Normal and Tumor Bearing Mice All animal studies were performed in compliance with the UK Animals (Scientific Procedures) Act of 1986 and the Code of Practice for the Housing and Care of Animals used in Scientific Procedures (Home Office, UK).

A. Biodistribution on Non Tumour Bearing Mice 12 female Balb/c mice were injected intravenously with 0.2 MBq of $^{111}$In labelled DTPA-AMB8LK, CHX-DTPA-AMB8LK or DOTA-AMB8LK (1.5 µg) in 50 µl of PBS. Groups of 4 animals were sacrificed by cervical dislocation after 24 hours, 48 hours and 72 hours. A sample of their blood, femur and muscle were dissected and weighed. Liver, lung, stomach, spleen, intestine and kidneys were also collected. The activity in each sample was counted in a gamma counter together with dilutions of the injected $^{111}$In-Ab. The uptake was expressed as a percentage of the injected dose per gram of tissue for the blood, bone and muscle, while for all other organs, the activity was expressed as a percentage of the injected dose per organ.

B. In vivo Tumour Model: Biodistribution on CAPAN-1 Tumours Bearing Mice

Tumours were initially established in donor mice by subcutaneous injection of 0.5×10⁶ CAPAN-1 cells in 100 µl of PBS into the flank of nu/nu mice (Cancer Research-UK, London). After a 5 month period, the tumours were minced and transplanted into 24 nu/nu mice and allowed to grow for 15 to 21 days. Mice were injected i.v. with the radiolabelled antibodies: 0.2 MBq (1.5 µg) for the $^{111}$In- and 0.4 MBq (3 µg) for the $^{90}$y-labelled antibodies, 50 µl/PBS. At selected time points, groups of 4 animals were killed by cervical dislocation and the organs were resected: samples of blood, bone, and muscle and the entire tumour, liver, lung, stomach, spleen, intestine, kidneys and pancreas. The data was processed as described above for the non-tumour bearing mice.

Figure 12:
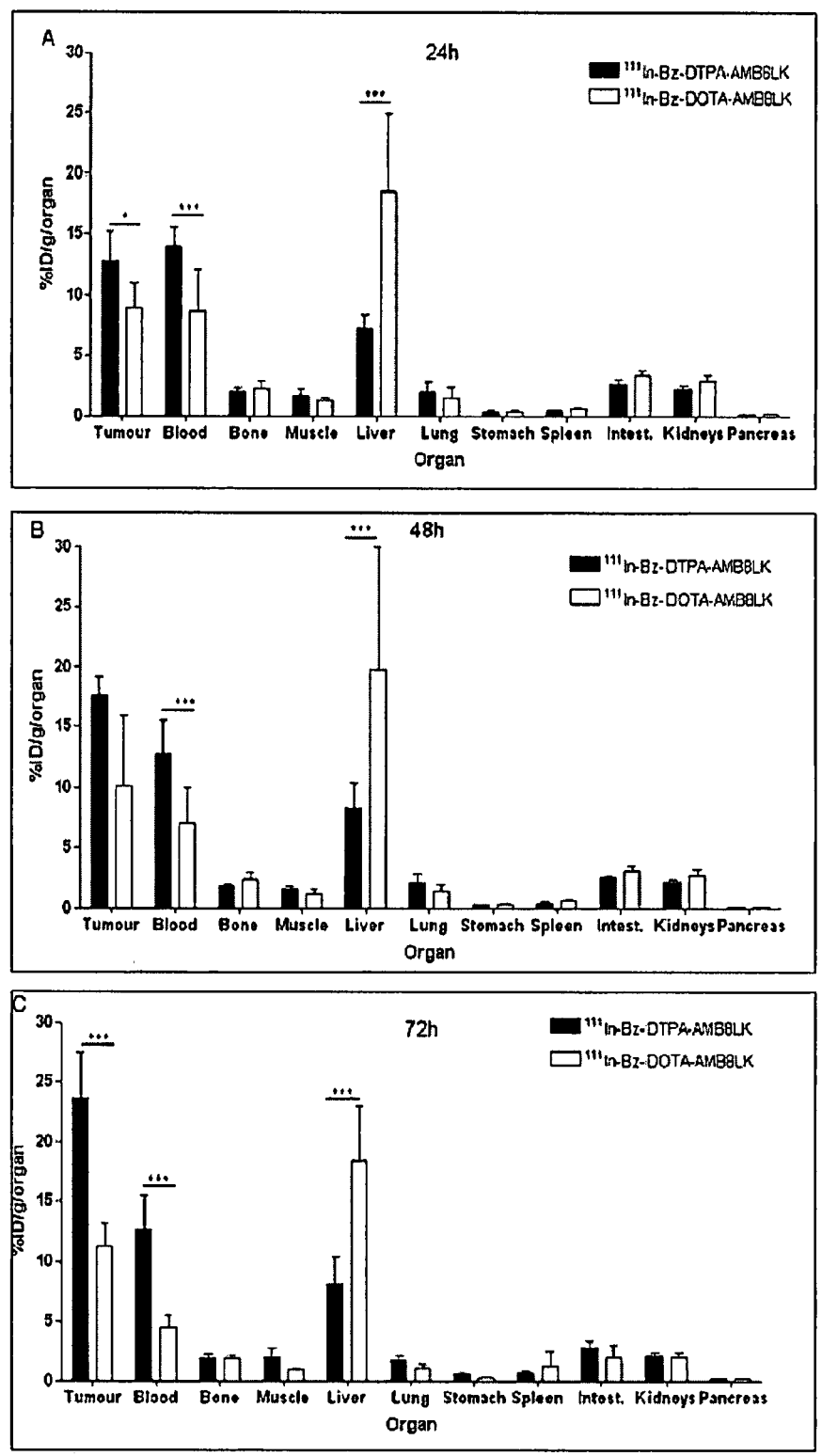
FIGS. 12 A, B and C are graphs showing the biodistribution in CAPAN-1 tumor bearing mice of $^{111}$In-DTPA-AMB8LK and $^{111}$In-DOTA-AMB8LK. 0.2 MBq of indium-labelled Bz-DTPA-AMB8LK or Bz-DOTA-AMB8LK were intravenously injected in CAPAN-1 tumor bearing mice. Animals were sacrificed at different time points and the organs were collected for activity counting. Data are expressed as percentage of the injected dose per organ (or per gram of tissue for the tumor, blood, muscle and bone). Error bars represent SD, n=4 per group. The abbreviation Intest stands for intestine. Graph A is the distribution 24 hours after injection. Graph B is the distribution 48 hours after injection. Graph C is the distribution 72 hours after injection.
Figure 13:
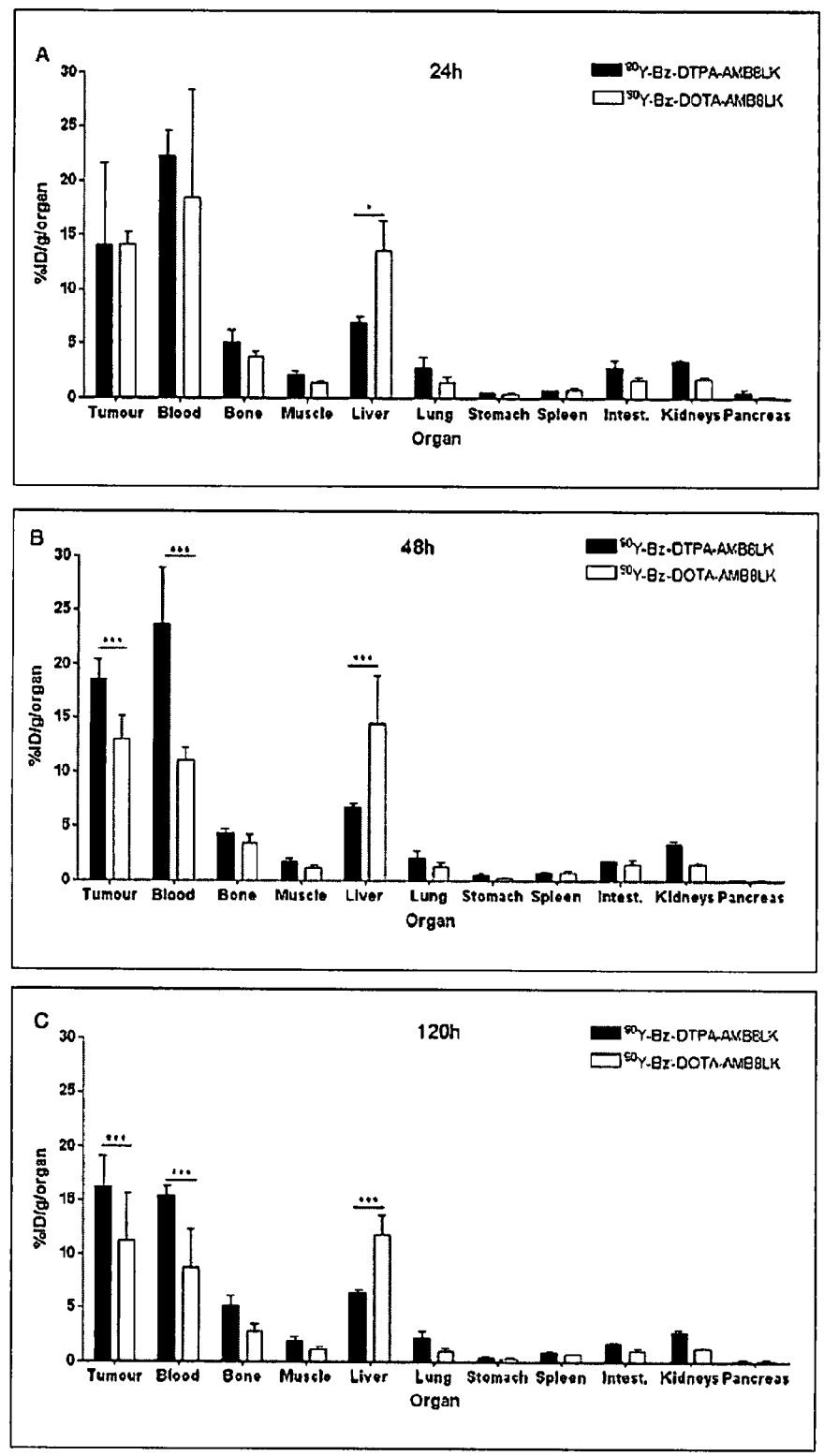
FIGS. 13 A, B and C are graphs showing the biodistribution in CAPAN-1 tumor bearing mice of $^{90}$Y-Bz-DTPA-AMB8LK and $^{90}$Y-Bz-DOTA-AMB8LK. 0.4 MBq of yttrium-labelled Bz-DTPA-AMB8LK or Bz-DOTA-AMB8LK were intravenously injected in CAPAN-1 tumor bearing mice. Animals were sacrificed at different time points and the organs were collected for activity counting. Data are expressed as percentage of the injected dose per organ (or per gram of tissue for the tumor, blood, muscle and bone). Error bars represent SD, n=4 per group. The abbreviation Intest stands for intestine. Graph A is the distribution 24 hours after injection. Graph B is the distribution 48 hours after injection. Graph C is the distribution 120 hours after injection.

Tumour uptake of $^{111}$In-DTPA-AMB8LK was 12.8±2.4% of the injected dose (ID) per gram of organ 24 hours after the injection. After 72 hours it reached 23.6±3.9% (Table 3 and FIG. 12). The tumour targeting of the $^{111}$In-labelled-DOTA conjugate was inferior to that of the DTPA: starting from 8.9±2.0% after 24 hours, it was only 11.2±1.9% of the ID/g after three days. As for the $^{90}$y-labelled DTPA-conjugate, uptake by the tumour was 14.0±7.5% of the ID/g after 24 hours. It peaked at 18.6±1.9% after 48 hours, then declined to 16.2±2.9% at the last time point of this experiment, 120 hours (Table 4 and FIG. 13). Tumour uptake of $^{90}$y-DOTA-AMB8LK was 14.1±1.2% at 24 hours and declined to 11.2±4.5% after 120 h.

Liver uptake of both compounds, labelled with indium or yttrium, was very similar to that obtained in non-tumour bearing mice. It showed again a liver uptake of the DOTA-conjugate more than twice as high as that of DTPA (Tables 3 and 4 and FIGS. 12 and 13).

TABLE 3

Biodistribution of $^{111}$In-labelled Bz-DTPA- and Bz-DOTA-AMB8LK in CAPAN-1 tumour bearing mice.

| | Bz-DTPA-AMB8LK Mean ± SD, n = 4 | | | Bz-DOTA-AMB8LK Mean ± SD, n = 4 | | |
|---|---|---|---|---|---|---|
| | 24 h | 48 h | 72 h | 24 h | 48 h | 72 h |
| Blood | 14.0 ± 1.6 | 12.7 ± 2.8 | 12.7 ± 2.8 | 8.6 ± 3.4 | 7.0 ± 3.0 | 4.5 ± 1.0 |
| Bone | 2.0 ± 0.4 | 1.8 ± 0.2 | 1.8 ± 0.4 | 2.3 ± 0.6 | 2.2 ± 0.6 | 1.8 ± 0.3 |
| Muscle | 1.7 ± 0.5 | 1.6 ± 0.2 | 2.0 ± 0.7 | 1.3 ± 0.2 | 1.2 ± 0.4 | 0.9 ± 0.1 |
| Tumour | 12.8 ± 2.4 | 17.6 ± 1.5 | 23.6 ± 3.9 | 8.9 ± 2.0 | 12.6 ± 3.9 | 11.2 ± 1.9 |
| Liver | 7.2 ± 1.2 | 8.4 ± 2.0 | 8.2 ± 2.1 | 18.6 ± 6.3 | 19.7 ± 10.2 | 18.4 ± 4.7 |
| Lung | 2.0 ± 0.9 | 2.1 ± 0.7 | 1.6 ± 0.4 | 1.5 ± 1.0 | 1.4 ± 0.5 | 1.0 ± 0.4 |
| Stomach | 0.4 ± 0.1 | 0.3 ± 0.1 | 0.5 ± 0.2 | 0.4 ± 0.1 | 0.3 ± 0.1 | 0.3 ± 0.1 |
| Spleen | 0.6 ± 0.1 | 0.4 ± 0.1 | 0.6 ± 0.2 | 0.6 ± 0.1 | 0.6 ± 0.1 | 1.2 ± 1.2 |
| Intestine | 2.6 ± 0.4 | 2.5 ± 0.1 | 2.7 ± 0.1 | 3.4 ± 0.4 | 3.1 ± 0.4 | 2.0 ± 1.0 |
| Kidneys | 2.3 ± 0.2 | 2.1 ± 0.2 | 2.1 ± 0.3 | 2.9 ± 0.5 | 2.7 ± 0.5 | 2.0 ± 0.3 |
| Pancreas | 0.2 ± 0.0 | 0.1 ± 0.0 | 0.1 ± 0.0 | 0.2 ± 0.0 | 0.1 ± 0.0 | 0.1 ± 0.0 |

Values are presented as the mean percentage of the injected dose per organ (or per 9 of tissue for the blood, the bone, the muscle and the tumour)±standard deviation, n=4 for each group.

TABLE 4

Biodistribution of $^{90}$y-labelled Bz-DTPA- and Bz-DOTA-AMB8LK in CAPAN-1 tumour bearing mice.

| | Bz-DTPA-AMB8LK Mean ± SD, n = 4 | | | Bz-DOTA-AMB8LK Mean ± SD, n = 4 | | |
|---|---|---|---|---|---|---|
| | 24 h | 48 h | 120 h | 24 h | 48 h | 120 h |
| Blood | 22.3 ± 2.4 | 23.6 ± 5.3 | 15.4 ± 0.8 | 18.5 ± 10.0 | 11.0 ± 1.1 | 8.7 ± 3.5 |
| Bone | 5.1 ± 1.1 | 4.4 ± 0.4 | 5.2 ± 0.8 | 3.8 ± 0.5 | 3.4 ± 0.9 | 2.7 ± 0.8 |
| Muscle | 2.1 ± 0.4 | 1.7 ± 0.3 | 1.9 ± 0.4 | 1.4 ± 0.2 | 1.2 ± 0.2 | 1.1 ± 0.3 |
| Tumour | 14.0 ± 7.5 | 18.6 ± 1.9 | 16.2 ± 2.9 | 14.1 ± 1.2 | 12.9 ± 2.3 | 11.2 ± 4.5 |
| Liver | 6.9 ± 0.6 | 6.7 ± 0.4 | 6.4 ± 0.3 | 13.6 ± 2.8 | 14.5 ± 4.5 | 11.8 ± 1.8 |
| Lung | 2.7 ± 1.0 | 2.1 ± 0.6 | 2.2 ± 0.6 | 1.4 ± 0.5 | 1.3 ± 0.4 | 1.0 ± 0.2 |
| Stomach | 0.5 ± 0.1 | 0.6 ± 0.2 | 0.3 ± 0.1 | 0.3 ± 0.2 | 0.3 ± 0.1 | 0.2 ± 0.1 |
| Spleen | 0.8 ± 0.0 | 0.7 ± 0.1 | 0.8 ± 0.1 | 0.7 ± 0.2 | 0.8 ± 0.1 | 0.7 ± 0.1 |
| Intestine | 2.9 ± 0.7 | 1.9 ± 0.0 | 1.6 ± 0.2 | 1.7 ± 0.3 | 1.6 ± 0.3 | 1.0 ± 0.1 |
| Kidneys | 3.4 ± 0.2 | 3.4 ± 0.3 | 2.8 ± 0.1 | 1.8 ± 0.2 | 1.6 ± 0.2 | 1.2 ± 0.1 |
| Pancreas | 0.4 ± 0.3 | 0.1 ± 0.0 | 0.1 ± 0.0 | 0.1 ± 0.0 | 0.1 ± 0.1 | 0.1 ± 0.1 |

Values are presented as the mean percentage of the injected dose per organ (or per g of tissue for the blood, the bone, the muscle and the tumour)±standard deviation, n=4 for each group.

The uptake of the radiolabelled antibodies in the stomach, spleen and pancreas was very low (less than 1% of the ID). Although the bone uptake was <5% of the ID for the two conjugates at all time points, significant differences were noticed between the uptake of the indium and yttrium-labelled-DTPA-antibody: the bone uptake of the $^{90}$y-DTPA-AMB8LK was greater than that of the $^{111}$In-DTPA-AMB8LK at 24 hours and 48 hours time points (P<0.001). No such difference occurred between the yttrium- and indium-labelled-DOTA-antibody: P<0.05 at 24 hours but no significant difference at 48 hours.

C. Imaging of $^{111}$In-DTPA-AMB8LK in Mouse

One CAPAN-1 tumour bearing mouse was injected i.v. with 20 MBq of $^{111}$In-labelled DTPA-AMB8LK. At required time points, the mouse was anesthetised by ketamine/xylazine (2/1) injection then imaged during 20 is minutes with a NanoSPECT/CT apparatus (Bioscan). The SPECT reconstructions had a voxel size of 0.4 mm, the CT of 0.2 mm.

Figure 14:
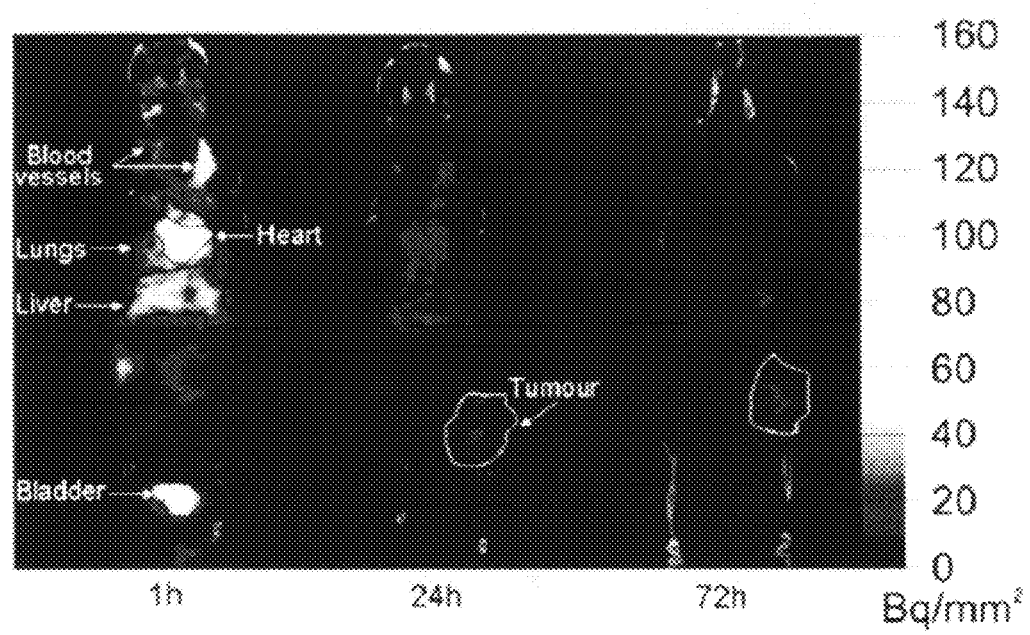
FIG. 14 are three images of a CAPAN-1 tumor bearing mouse injected with $^{111}$In-DOTA-AMB8LK. A CAPAN-1 tumor bearing nude mouse was intravenously injected with 20 MBq of $^{111}$In-DTPA-AMB8LK then imaged at different time points. This figure shows the scans done 1, 24 and 72 hours after injection, The same scale of radioactivity levels was applied to the three images but taken into account the decay of the indium, the radioactivity level in the tumor after 72 hours is superior to that after 24 hours.
Figure 15:
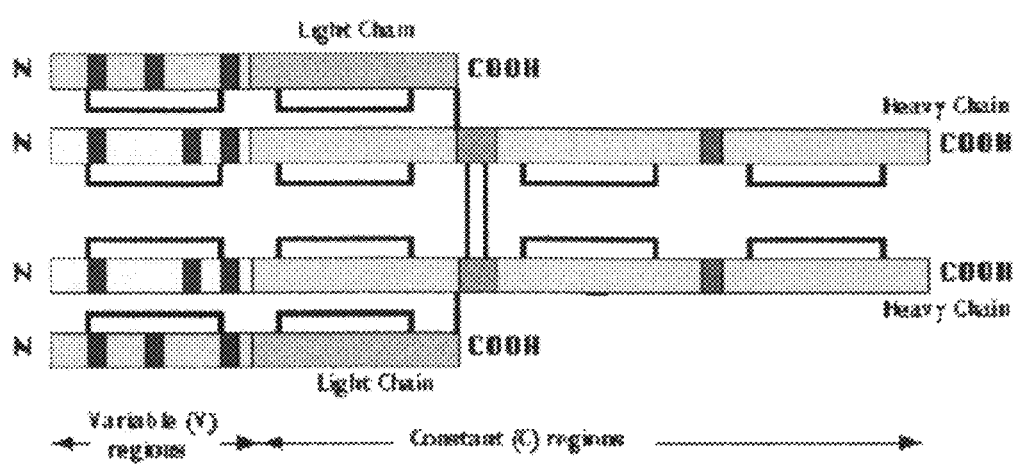
FIG. 15 is a diagram of the monoclonal antibody of the present invention.

FIG. 14 shows some images, wherein the scale of the radioactivity levels and some of the organs are indicated. Decay correction was applied to get all of the studies at the same level since the half-life of indium is 67.2 hours. 1 hour after injection, the majority of the injected compound was located in the bladder and the heart with also important uptake in the liver and lungs. As can be seen and as already observed in the biodistribution experiments reported above, significant tumour accumulation occurred 24 hours after the compound injection was injected with still some localization in the heart and liver. Radioactivity in the tumour is still present after 72 hours.

D. Statistical Analysis

Biodistribution data were analysed with the GraphPad Prism software (San Diego, Calif.). Data are expressed as mean±SD and evaluated for statistical significance with two-way ANOVA followed by a Bonferroni post test. The criteria of significance were set as *P<0.05, P<0.01 and *P<0.001.

EXAMPLE 9

In Vitro Assessment of the ADCC of Chimeric AMB8LK

The ADCC activity of the chimeric AMB8LK antibody was measured on the non-labeled antibody set forth above, using the following protocol: CAPAN-1 cells were stained with carboxyfluorescein diactete succinimidyl ester, which is a reagent for the analysis of cellular proliferation. Basically, peripheral blood mononuclear cells were isolated from heparinized blood following the ACTG PBMC Consensus Method. The cells were harvested from the interface of a ficoll layer and were washed twice with RPMI 1640 medium. After the last wash, the cells were transferred to a test tube and a viable cell count was undertaken. The cells were then spun at 800×g for 10 minutes and the RPMI medium was removed. The cells were then resuspended in 2.5 ml of a 0.1% BSA/PBS solution at room temperature, then were centrifuged at 800×g for 10 minutes and the supernatant was decanted. 250 µl of a 0.1% to 0.5% BSA in PBS was added to the cell pellet and the cells were then suspended.

Capan-1 cells were then stained with diluted CFSE (CarboxyFluorescein diacetate Succinimidyl Ester) for 15 min at 37° C. Media was then added in a large excess to complex the unbound CFSE. Then, cells were washed 3 times with PBS and resuspended in complete media (1 ml/$10^6$ cells) that is RPMI, 10% human AB sera, 1% L-Glutamine, 1% Hepes buffer and 1% penicillin/streptomycin. 1 ml of cells were used per well of a 24-well plate. Addition of PBMC at a PBMC:cells ratio ranging from 5:1 to 50:1 and of the AMB8LK antibody (1 to 10 µg/well by example) was done. The cells were centrifuged at low speed (1000 rpm) and then left to incubate for 30 min at 37° C. The 7AAD (7-aminoactinomycin D) stain was then added and the cells were analysed on a cell cytometer. Results showed that the AMB8LK antibody has ADCC activity on Capan-1 cells.

The same experiments may be carried out with other chimeric monoclonal antibody or with antibody-like molecules of the invention, disclosed in the present specification, to assess in vitro ADCC activity.

EXAMPLE 10

Therapeutic Effects on Tumor Growth Using Radiolabelled Chimeric Monoclonal AMB8LK Antibodies Monoclonal antibodies AMB8LK were produced as set forth above in Example I, conjugated as in Example III and radiolabeled as in Example IV above.

LD50 Determination

Firstly, a radioactive dose escalation study to determine the $LD_{50}$ is done using 6 groups of 4 mice: chimeric AMB8LK antibody is radiolabeled using yttrium-90 at various specific activities, so as to inject in each mouse the same antibody amount: 49 MBq of $^{90}$y/mg of antibody, 86 MBq of $^{90}$y/mg of antibody, 123 MBq of $^{90}$y/mg of antibody, 185 MBq of $^{90}$y/mg of antibody and 246 MBq of $^{90}$y/mg of antibody. Then, group I mice are injected with 30 µg of cold antibody, group II mice with 30 µg of chimeric AMB8LK radiolabeled at a specific activity of 49 MBq of $^{90}$y/mg of antibody (40 µCi/mouse), group III mice with 30 µg of chimeric AMB8LK radiolabeled at a specific activity of 86 MBq of $^{90}$y/mg of antibody (70 µCi/mouse), group IV mice with 30 µg of chimeric AMB8LK radiolabeled at a specific activity of 123 MBq of $^{90}$y/mg of antibody (100 µCi/mouse), group V mice with 30 µg of chimeric AMB8LK radiolabeled at a specific activity of 185 MBq of $^{90}$y/mg of antibody (150 µCI/mouse) and group VI with 30 µg of chimeric AMB8LK radiolabeled at a specific activity of 246 MBq of $^{90}$y/mg of antibody (200 µCi/mouse). Mice are weighed twice a week, during 8 weeks after the injection and tumour size is recorded twice a week. If a mouse dies during the observation period, an autopsy is performed to determine if the death is due to radiotoxicity.

Tumor Volume Reduction

Once the $LD_{50}$ is established, the therapeutic efficacy of the chimeric AMB8LK antibody can be studied using four specific activities, all below the $LD_{50}$. $5\times10^6$ CAPAN-1 cells are injected into Balb/c/nu/nu mice as described in a previous example to establish tumour in Balb/c/nu/nu mice. Once the tumour reaches the volume of 200 mm$^3$, experiments can begin. Four groups of 6 mice are monitored for 84 days and are sacrificed, if the tumor has a volume of >1000 mm$^3$.

Group I-mice are administered with 30 µg of the chimeric monoclonal antibody of AMB8LK of the present invention, radiolabeled with yttrium at a specific activity n°1.

Group II-mice are injected with 30 µg of the chimeric monoclonal antibody of AMB8LK of the present invention, radiolabeled with yttrium at a specific activity n°2.

Group III-mice are injected with 30 µg of the chimeric monoclonal antibody of AMB8LK of the present invention, radiolabeled with yttrium at a specific activity n°3.

Group IV-mice are injected with 30 µg of the chimeric monoclonal antibody of AMB8LK of the present invention, radiolabeled with yttrium at a specific activity n°4.

The above experiment shows that there is effective tumor reduction using the radiolabeled antibodies of the present invention and in vitro ADCC activity of the AMB8LK antibody.

The same experiments may be carried out with other chimeric monoclonal antibody or with antibody-like molecules of the invention, and disclosed in the present specification.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. A chimeric anti-ferritin monoclonal antibody that binds both human acidic and basic ferritin, comprising:
   (a) two light chains, each consisting of a polypeptide comprising SEQ ID NO:2 or a variant having a degree of similarity of at least 90% with SEQ ID NO:2, wherein the CDR1, CDR2 and CDR3 domains of said variant consist respectively of SEQ ID NO:20, SEQ ID NO:22 and SEQ ID NO:24; and
   (b) two heavy chains, each consisting of a polypeptide comprising SEQ ID NO:4 or a variant having a degree of similarity of at least 90% with SEQ ID NO:4, wherein the CDR1, CDR2 and CDR3 domains of said variant consist respectively of SEQ ID NO:30, SEQ ID NO:28 and SEQ ID NO:26.

2. The chimeric anti-ferritin monoclonal antibody according to claim 1, wherein the constant region of each of said two light chains is a kappa region as defined in SEQ ID NO:12.

3. The chimeric anti-ferritin monoclonal antibody according to claim 1, wherein said polypeptide comprising SEQ ID NO:2 or said variant thereof further comprises SEQ ID NO:12; and wherein said polypeptide comprising SEQ ID NO: 4 or said variant thereof further comprises SEQ ID NO: 8.

4. The chimeric anti-ferritin monoclonal antibody according to claim 1, wherein said polypeptide comprising SEQ ID NO:2 or said variant thereof further comprises SEQ ID NO:12; and wherein said polypeptide comprising SEQ ID NO: 4 or said variant thereof further comprises SEQ ID NO: 10.

5. A fragment of a monoclonal chimeric antibody according to claim 1, which specifically binds to both human acidic and basic ferritin.

6. The fragment according to claim 5, wherein said fragment is a Fv fragment.

7. The Fv fragment according to claim 6, consisting of SEQ ID NO:2 or a variant having a degree of similarity of at least 90% with SEQ ID NO:2, wherein the CDR1, CDR2 and CDR3 domains of said variant consist respectively of SEQ ID NO:20, SEQ ID NO:22 and SEQ ID NO:24, non-covalently associated with SEQ ID NO:4 or a variant having a degree of similarity of at least 90% with SEQ ID NO:4, wherein the CDR1, CDR2 and CDR3 domains of said variant consist respectively of SEQ ID NO:30, SEQ ID NO:28 and SEQ ID NO:26.

8. The fragment according to claim 5, wherein said fragment is a Fab fragment.

9. The Fab fragment according to claim 8 consisting of:
   (a) a polypeptide consisting of SEQ ID NO:2 or a variant having a degree of similarity of at least 90% with SEQ ID NO:2, wherein the CDR1, CDR2 and CDR3 domains of said variant consist respectively of SEQ ID NO:20, SEQ ID NO:22 and SEQ ID NO:24, directly linked to SEQ ID NO:12; and
   (b) a polypeptide consisting of SEQ ID NO:4 or a variant having a degree of similarity of at least 90% with SEQ ID NO:4, wherein the CDR1, CDR2 and CDR3 domains of said variant consist respectively of SEQ ID NO:30, SEQ ID NO:28 and SEQ ID NO:26, directly linked to SEQ ID NO:6.

10. A bispecific monoclonal antibody comprising at least one Fab fragment according to claim 9.

11. A trispecific monoclonal antibody comprising at least one Fab fragment according to claim 9.

12. The bispecific monoclonal antibody according to claim 10 or the trispecific monoclonal antibody according to claim 11, wherein at least one Fab interacts with an antigen different from the human ferritin.

13. The bispecific monoclonal antibody according to claim 10 or the trispecific monoclonal antibody according to claim 11, wherein at least one Fab interacts with an epitope different from the epitope common to human acidic and basic ferritin.

14. A bifunctional monoclonal antibody comprising a Fab fragment according to claim 9, wherein said antibody is linked to a ligand.

15. A scFv molecule consisting of (a) a variable light (VL) domain consisting of a polypeptide as defined in SEQ ID NO:2 or a variant having a degree of similarity of at least 90% with SEQ ID NO:2, wherein the CDR1, CDR2 and CDR3 domains of said variant consist respectively of SEQ ID NO:20, SEQ ID NO:22 and SEQ ID NO:24; linked to (b) a variable heavy (VH) domain consisting of a polypeptide as defined in SEQ ID NO:4 or a variant having a degree of similarity of at least 90% with SEQ ID NO:4, wherein the CDR1, CDR2 and CDR3 domains of said variant consist respectively of SEQ ID NO:30, SEQ ID NO:28 and SEQ ID NO:26, and wherein said scFv molecule specifically binds to both human acidic and basic ferritin.

16. The scFv molecule according to claim 15, wherein said VL domain is SEQ ID NO:2 and said VH domain is SEQ ID NO:4.

17. A Bis-scFv or a diabody comprising at least one scFv according to claim 15.

18. An anti-ferritin monoclonal antibody that binds both human acidic and basic ferritin comprising as a light chain, from the N-terminal to the C-terminal, SEQ ID NO:2 and SEQ ID NO:12, and as a heavy chain, from the N-terminal to the C-terminal, SEQ ID NO:4 and SEQ ID NO:18.

19. The chimeric anti-ferritin monoclonal antibody of claim 1 further comprising a radioisotope conjugated to said antibody.

20. The chimeric anti-ferritin monoclonal antibody according to claim 19, wherein said radioisotope is selected from the group consisting of alpha-, beta-, gamma-, beta-gamma- and alpha-beta-emitting radioisotopes.

21. The chimeric anti-ferritin monoclonal antibody according to claim 19, wherein said radioisotope is conjugated through a chelating agent conjugated to said antibody.

22. The chimeric anti-ferritin monoclonal antibody according to claim 21, wherein said chelating agent is selected from the group consisting of diethylenetriaminepentaacetic acid (DTPA); 1,4,7,10-tetraazacyclododecane-1,4,7,10-tetraacetic acid (DOTA); 1,3-bis[N—[N—(2-aminoethyl)-2-aminoethyl]-propane-N,N,N',N'',N''',N''''',N'''''-octaacetic acid (LiLo); N—(S-acetylmercaptoacetyl)(p-NCS)phenylalanylglycylglycine ethyl ester; 5,7-dioxo-1,11-(carboxymethyl)-1,4,8,11-tetraazacyclotridecane; 1,4,7,10-tetraazacyclotridecane-N,N',N'',N''''-tetra-acetic acid (TRITA); 1, 4, 8, 11-tetraaxacyclootetra-decane-N, N', N'', N''''-tetraacetic acid (TETA); and 1,5,9,13-tetraazacyclohexadecane-N,N',N'''',N'''''-tetraacetic acid.

23. The chimeric anti-ferritin monoclonal antibody of claim 1 further comprising a drug conjugated to said antibody.

24. The chimeric anti-ferritin monoclonal antibody according to claim 23, wherein said drug is a pyrimidine drug.

25. The chimeric anti-ferritin monoclonal antibody according to claim 24, wherein said pyrimidine drug is selected from the group consisting of fluorouracil, capecitabine, cytarabine, floxuridine and gemcitabine.

26. A pharmaceutical composition comprising, as an active principle, a chimeric anti-ferritin monoclonal antibody according to claim 1 or a functional fragment thereof and a pharmaceutically acceptable carrier.

27. The pharmaceutical composition according to claim 26, wherein said chimeric anti-ferritin monoclonal antibody comprises two light chains, each consisting of a polypeptide comprising SEQ ID NO:2 and two heavy chains, each consisting of a polypeptide comprising SEQ ID NO:4.

28. The pharmaceutical composition according to claim 26, further comprising a pyrimidine drug selected from the group consisting of fluorouracil, capecitabine, cytarabine, floxuridine and gemcitabine.

29. A method of treating a cancer selected from the group consisting of pancreatic cancer, Hodgkins lymphoma, Kaposi sarcoma and hepatocellular carcinoma, comprising the step of administering a composition according to claim 26 and a drug, radioactive material, toxin, immune killer cell or a combination thereof to a mammal in need of such treatment, thereby treating said cancer in said mammal.

30. A method of treating a cancer selected from the group consisting of pancreatic cancer, Hodgkins lymphoma, Kaposi sarcoma and hepatocellular carcinoma comprising the step of administering a composition according to claim 27 and a drug, radioactive material, toxin, immune killer cell or a combination thereof to a mammal in need of such treatment, thereby treating said cancer in said mammal.

31. The method of treating a cancer according to claim 30, wherein said light chain polypeptide comprises, from the N-terminal to the C-terminal, SEQ ID NOs: 2 and 12, and said heavy chain polypeptide comprises, from the N-terminal to the C-terminal, SEQ ID NOs: 4 and 8 or SEQ ID NOs: 4 and 10.

32. The method according to claim 30, wherein said drug is a pyrimidine drug and said cancer is pancreatic cancer.

33. The method according to claim 32, wherein said pyrimidine drug is selected from the group consisting of fluorouracil, capecitabine, cytarabine, floxuridine and gemcitabine.

34. The method according to claim 33, wherein said pyrimidine drug is gemcitabine.

35. The method according to claim 30, wherein said radioactive material is selected from the group consisting of alpha-, beta-, gamma-, beta-gamma- and alpha-beta-emitting radioisotopes.

36. A chimeric anti-ferritin monoclonal antibody, which binds both human acidic and basic ferritin, comprising:
(a) two heavy chains each encoded by a polynucleotide consisting essentially of SEQ ID NO: 3, optionally linked to a polynucleotide encoding a CH1 constant region linked to a polynucleotide encoding a human Fc region, and
(b) two light chains each encoded by a polynucleotide consisting essentially of SEQ ID NO: 1, optionally linked to a polynucleotide encoding a kappa region.

37. The chimeric anti-ferritin monoclonal antibody according to claim 36, wherein said kappa region is as defined in SEQ ID NO:11.

38. The chimeric anti-ferritin monoclonal antibody according to claim 36, wherein said CH1 constant region is as defined in SEQ ID NO:5.

39. The chimeric anti-ferritin monoclonal antibody according to claim 36, wherein SEQ ID NO: 3 is linked from 5' to 3' to a polynucleotide encoding a CH1 constant region linked to a polynucleotide encoding a human Fc region, and wherein SEQ ID NO:1 is linked from 5' to 3' to a polynucleotide encoding a kappa region.

40. The chimeric anti-ferritin monoclonal antibody according to claim 39, wherein said polynucleotide encoding a CH1 constant region linked to a polynucleotide encoding a human Fc region is a human gamma 4 constant region as defined in SEQ ID NO:9, and said polynucleotide encoding a kappa region is as defined in SEQ ID NO:11.

41. The chimeric anti-ferritin monoclonal antibody according to claim 39, wherein said polynucleotide encoding a CH1 constant region linked to a polynucleotide encoding a human Fc region is a human gamma 1 constant region as defined in SEQ ID NO:7, and said polynucleotide encoding a kappa region as defined in SEQ ID NO:11.

42. A chimeric anti-ferritin monoclonal antibody that binds both human acidic and basic ferritins, comprising:
   (a) two light chains, each consisting of a polypeptide comprising SEQ ID NO:2, or a variant having a degree of similarity of at least 95% with SEQ ID NO:2, wherein the CDR1, CDR2 and CDR3 domains of said variant consist respectively of SEQ ID NO:20, SEQ ID NO:22 and SEQ ID NO:24; and
   (b) two heavy chains, each consisting of a polypeptide comprising SEQ ID NO:4, or a variant having a degree of similarity of at least 95% with SEQ ID NO:4, wherein the CDR1, CDR2 and CDR3 domains of said variant consist respectively of SEQ ID NO:30, SEQ ID NO:28 and SEQ ID NO:26.

43. A chimeric anti-ferritin monoclonal antibody that binds both human acidic and basic ferritins, comprising:
   (a) two light chains, each consisting of a polypeptide comprising SEQ ID NO:2, or a variant having a degree of similarity of at least 98% with SEQ ID NO:2, wherein the CDR1, CDR2 and CDR3 domains of said variant consist respectively of SEQ ID NO:20, SEQ ID NO:22 and SEQ ID NO:24; and
   (b) two heavy chains, each consisting of a polypeptide comprising SEQ ID NO:4, or a variant having a degree of similarity of at least 98% with SEQ ID NO:4, wherein the CDR1, CDR2 and CDR3 domains of said variant consist respectively of SEQ ID NO:30, SEQ ID NO:28 and SEQ ID NO:26.

44. The chimeric anti-ferritin monoclonal antibody according to claim 1, wherein the CH1 domain of said heavy chain polypeptide is as defined in SEQ ID NO:6.

45. The chimeric anti-ferritin monoclonal antibody according to claim 1, wherein said light chain polypeptide comprises, from the N-terminal to the C-terminal, SEQ ID NO:2 and SEQ ID NO:12, and said heavy chain polypeptide comprises, from the N-terminal to the C-terminal, SEQ ID NO: 4 and SEQ ID NO: 10.

46. A Fv fragment consisting of SEQ ID NO:2 non-covalently associated with SEQ ID NO:4.

47. A Fab fragment consisting of (a) a polypeptide consisting from the N-terminal to the C-terminal of SEQ ID NO:2 directly linked to SEQ ID NO:12 and (b) a polypeptide consisting from the N-terminal to the C-terminal of SEQ ID NO:4 directly linked to SEQ ID NO:6.

48. The bispecific monoclonal antibody according to claim 14, wherein said ligand is a cytokine or a receptor.

49. The trispecific monoclonal antibody comprising a Fab fragment according to claim 11, wherein said antibody is linked to a ligand.

50. The trispecific monoclonal antibody according to claim 49, wherein said ligand is a cytokine or a receptor.

51. A polynucleotide encoding a chimeric anti-ferritin monoclonal antibody that binds both human acidic and basic ferritin, comprising:
   (a) two light chains, each consisting of a polypeptide comprising SEQ ID NO:2 or a variant having a degree of similarity of at least 90% with SEQ ID NO:2, wherein the CDR1, CDR2 and CDR3 domains of said variant consist respectively of SEQ ID NO:20, SEQ ID NO:22 and SEQ ID NO:24; and
   (b) two heavy chains, each consisting of a polypeptide comprising SEQ ID NO:4 or a variant having a degree of similarity of at least 90% with SEQ ID NO:4, wherein the CDR1, CDR2 and CDR3 domains of said variant consist respectively of SEQ ID NO:30, SEQ ID NO:28 and SEQ ID NO:26.

* * * * *